(12) United States Patent
Aebersold et al.

(10) Patent No.: US 7,473,535 B2
(45) Date of Patent: Jan. 6, 2009

(54) CHEMICAL REAGENTS AND METHODS FOR DETECTION AND QUANTIFICATION OF PROTEINS IN COMPLEX MIXTURES

(75) Inventors: Rudolf H. Aebersold, Mercer Island, WA (US); Patricia Q. Bottari, Seattle, WA (US); Michael H. Gelb, Seattle, WA (US); Frantisek Turecek, Seattle, WA (US)

(73) Assignees: The Institute for Systems Biology, Seattle, WA (US); University of Washington, Seattle, WA (US)

( * ) Notice: Subject to any disclaimer, the term of this patent is extended or adjusted under 35 U.S.C. 154(b) by 213 days.

(21) Appl. No.: 10/225,447

(22) Filed: Aug. 20, 2002

(65) Prior Publication Data

US 2004/0038319 A1 Feb. 26, 2004

(51) Int. Cl.
   *G01N 33/53* (2006.01)
   *A61K 38/00* (2006.01)
   *C07K 1/00* (2006.01)

(52) U.S. Cl. .......... 435/7.5; 514/44; 530/300; 530/350; 530/403

(58) Field of Classification Search ............ 435/6, 435/23; 530/350; 536/23.1, 25.3
See application file for complete search history.

(56) References Cited

U.S. PATENT DOCUMENTS

| | | | |
|---|---|---|---|
| 5,143,854 A | 9/1992 | Pirrung et al. | |
| 5,405,783 A | 4/1995 | Pirrung et al. | |
| 5,489,678 A | 2/1996 | Fodor et al. | |
| 5,643,722 A | 7/1997 | Rothschild et al. | |
| 5,917,016 A | 6/1999 | Holmes | |
| 5,986,076 A * | 11/1999 | Rothschild et al. | 536/22.1 |
| 6,406,863 B1 | 6/2002 | Zhu et al. | |
| 2003/0017507 A1 * | 1/2003 | Johnson | 435/7.5 |

FOREIGN PATENT DOCUMENTS

| EP | 1 215 501 | 6/2002 |
|---|---|---|
| WO | WO 00/11208 | 3/2000 |

OTHER PUBLICATIONS

Tureček, F. 2002. Mass Spectrometry in Coupling with Affinity Capture-Release and Isotope-Coded Affinity Tags for Quantitative Protein Analysis. J. Mass Spectrometry, vol. 37, pp. 1-14;Published on Line Dec. 21, 2001).*
Aebersold and Goodlett, "Mass Spectrometry in Proteomics," *Chem. Rev.* 101:269-295 (2001).
Atkinson et al., "Exchange reactions of carboxylic acid salts. A facile preparation of α-deuteriocarboxylic acids," *J. Am. Chem. Soc.* 90:498-499 (1968).
Bjellqvist et al., "The focusing positions of polypeptides in immobilized pH gradients can be predicted from their amino acid sequences," *Electrophoresis* 14:1023-1031 (1993).
Bruce et al., "High-Mass-Measurement Accuracy and 100% Sequence Coverage of Enzymatically Digested Bovine Serum Albumin from an ESI-FTICR Mass Spectrum," *Anal. Chem.* vol. 71, No. 14 pp. 2595-2599, American Chemical Press (1999).
Dorman and Prestwich, "Using photolabile ligands in drug discovery and development," *Trends Biotech.* 18:64-77 (2000).
Easterling et al., "Routine Part-per-Million Mass Accuracy for High-Mass Ions: Space-Charge Effects in MALDI FT-ICR," *Analytical Chemistry* vol. 71:624-632 (1999).
Felder et al., "Synthesis of a Photolabile 'Safety Catch' Linker of the 3'-Methoxybenzion Type," *First International Electric Conference on Synthetic Organic Chemistry (ECSOC-1)*, www.mdpi.org/esoc/, Sep. 1-30, 1997.
Gerber et al., "Design and synthesis of substrate an internal standard conjugates for profiling enzyme activity in the sanfilippo syndrome by affinity chromatography/electrospray ionization mass spectrometry," *Bioconj. Chem.* 12:603-615 (2001).
Glazer et al., *Laboratory Techniques in Biochemistry and Molecular Biology: Chemical Modification of Proteins*, Chapter 3, pp. 68-120, Elsevier Biomedical Press, New York (1975).
Goodlett et al., "Protein Identification with a Single Accurate Mass of a Cysteine-Containing Peptide and Constrained Database Searching," *Anal. Chem.* 72:1112-1118 (2000).
Greene and Wuts, *Protective Groups in Organic Synthesis* 2nd ed., John Wiley & Sons, New York (1991).
Griffin et al., "Advances in proteome analysis by mass spectrometry," *Current Opinion in Biotechnology* 12:607-612 (2001).
Gygi et al., "Quantitative analysis of complex protein mixtures using isotope-coded affinity tags," *Nature Biotechnology* 7:994-999 (1999).
Han et al., "Quantitative profiling of differentiation-induced microsomal proteins using isotope-coded affinity tags and mass spectrometry," *Nat. Biotech.* 19:946-951 (2001).
Hausch and Jaschke, "Multifunctional dinucleotide analogs for the generation of complex RNA conjugates," *Tetrahedron* 57:1261-1268 (2001).
Hermanson, *Bioconjugate Techniques* pp. 297-364, Academic Press, San Diego, (1996).
Hudecki and Pollina, "Mdx mouse as therapeutic model system: development and implementation of phenotypic monitoring," *Adv. Exp. Med. Biol.* 280:251-263 (1990).

(Continued)

*Primary Examiner*—Jon P Weber
*Assistant Examiner*—Kailash C Srivastava
(74) *Attorney, Agent, or Firm*—McDermott Will & Emery LLP

(57) ABSTRACT

The invention provides a reagent comprising an affinity tag, a detectable moiety, a linker, an isotope tag and a reactive group. The invention also provides methods of using a reagent of the invention. The methods can be used to label a polypeptide in a sample by contacting a sample with a reagent of the invention under conditions allowing the reactive group to bind to one or more polypeptides in the sample. The invention additionally provides methods of isolating, identifying and quantifying a polypeptide in a sample. The invention further provides methods of diagnosing a disease using a reagent of the invention.

38 Claims, 7 Drawing Sheets

OTHER PUBLICATIONS

Kinter and Sherman, *Protein Sequencing and Identification Using Tandem Mass Spectrometry*, John Wiley & Sons, New York (2000).

Link et al., "Direct analysis of protein complexes using mass spectrometry," *Nature Biotechnology* 17: 676-682, Nature America Inc.

Lochner et al., "General access to polyamines containing ethane-1, 2-diamine units: synthesis of unnatural homologues and isomeric $N^1$, 4-Di (4-coumaroyly) spermines," *Helv. Chim. Acta* 81:2270-2281 (1998).

Masselon et al., "Accurate mass multiplexed tandem mass spectrometry for high-throughput polypeptide identification from mixtures," *Anal. Chem.* 72:1918-1924 (2000).

Ohlendieck et al., "Dystrophin-glycoprotein complex is highly enriched in isolated skeletal muscle sarcolemma," *J. Cell Biol.* 112:135-148 (1991).

Ohlendieck and Campbell, Dystrophin constitutes 5% of membrane cytoskeleton in skeletal muscle, *FEBS Lett.* 283:230-234 (1991).

Olejnik et al., "Photocleavable biotin derivatives: a versatile approach for the isolation of biomolecules," *Proc. Natl. Acad. Sci. USA* 92:7590-7594 (1995).

Righetti et al., "Isoelectric focusing in immobilized pH gradients," *Methods. Enzymol.* 270:235-255 (1996).

Senter et al., "Novel photocleavable protein crosslinking reagents and their use in the preparation of antibody-toxin conjugates," *Photochem. Photobiol.* 42:231-237 (1985).

Sicinski et al., "The molecular basis of muscular dystrophy in the *mdx* mouse: a point mutation," *Science* 244:1578-1580 (1989).

Smolka et al., "Quantitative protein profiling using two-dimensional gel electrophoresis, isotope-coded affinity tag labeling, and mass spectrometry," *Molecular & Cellular Proteomics* 1:19-29 (2002).

Smolka et al., "Optimization of the isotope-coded affinity tag-labeling procedure for quantitative proteome analysis," *Anal. Biochem.* 297:25-31 (2001).

Ward, "The bromination of acids in the α-position," *J. Chem. Soc.* 1161-1165 (1922).

Wilmes and Winneswisser, "Preparation of Mono-$^{15}$N-Cyanogen and Mono-$^{13}$C-Cyanogen," *J. Labelled Compd. Radiopharm.* 31:1037-1040 (1992).

Yates, "Mass Spectrometry and the Age of the Proteome," *J. Mass Spect.* 33:1-19 (1998).

Yates et al., "Automated protein identification using microcolumn liquid chromatography-tandem mass spectrometry," *Methods Mol. Biol.* 112:553-569 (1999).

Zhou et al., "A systematic approach to the analysis of protein phosphorylation," *Nat. Biotechnol.* 19:375-378 (2001).

\* cited by examiner

Reaction Scheme

CHEMICAL REAGENTS AND METHODS FOR DETECTION AND QUANTIFICATION OF PROTEINS IN COMPLEX MIXTURES

This invention was made with government support under grant number GM60184 awarded by the National Institutes of Health. The government has certain rights to the invention.

BACKGROUND OF THE INVENTION

The invention is related to the field of analytical biochemistry, and more specifically to the field of quantitative proteomics.

Large scale sequencing of genomic DNA, cDNA and EST's (expressed sequence tags) has identified large numbers of genes. For some selected species, the complete genome sequences have been determined and, for others, EST sequence databases are assumed to contain sequence tags for the majority of genes for that species. For the species having complete genome sequences or substantial EST sequences available, essentially all the genes have been determined. Other genomic technologies including serial analysis of expressed genes (SAGE) and differential cDNA or oligonucleotide array analysis are capable of determining quantitative expression profiles of the expressed genes at the mRNA level in specific cells or tissues. Furthermore, comparative genomic analyses have identified genes that, if defective or aberrantly expressed, are the cause of genetic or somatic diseases.

From genomic analysis or the analysis of the expressed mRNA transcripts neither the quantity nor the structure, activity and state of modification of the translated protein products can be predicted. Recently developed mass spectrometric techniques allow the rapid identification of expressed proteins by the correlation of mass spectral data that are idiotypic for the sequence of a specific protein with the sequences contained in sequence databases.

A number of approaches have been used to address the needs of proteomics analysis, including the use of reagents that allow relative quantitation of proteins in a sample. However, none of the previously described methods can be used to determine the absolute quantity of the proteins in a sample. Furthermore, these methods do not allow the analysis to be focused on selected proteins such as those that are involved in specific diseases or those that are predicted or expected to be present based on circumstantial data or considerations.

Thus, there exists a need for reagents suitable for absolute quantitative analysis of protein samples as well as reagents suitable for analysis of selected proteins, which can be used as diagnostic or prognostic markers. The present invention satisfies these needs, and provides related advantages as well.

SUMMARY OF THE INVENTION

The invention provides a reagent comprising an affinity tag, a detectable moiety, a linker, an isotope tag and a reactive group, referred to herein as a VICAT reagent. The invention also provides methods of using a reagent of the invention. The methods can be used to label a polypeptide in a sample by contacting a sample with a reagent of the invention under conditions allowing the reactive group to bind to one or more polypeptides in the sample. The invention additionally provides methods of isolating, identifying and quantifying a polypeptide in a sample. The invention further provides methods of diagnosing a disease using a reagent of the invention.

DETAILED DESCRIPTION OF THE INVENTION

Figure 1A:
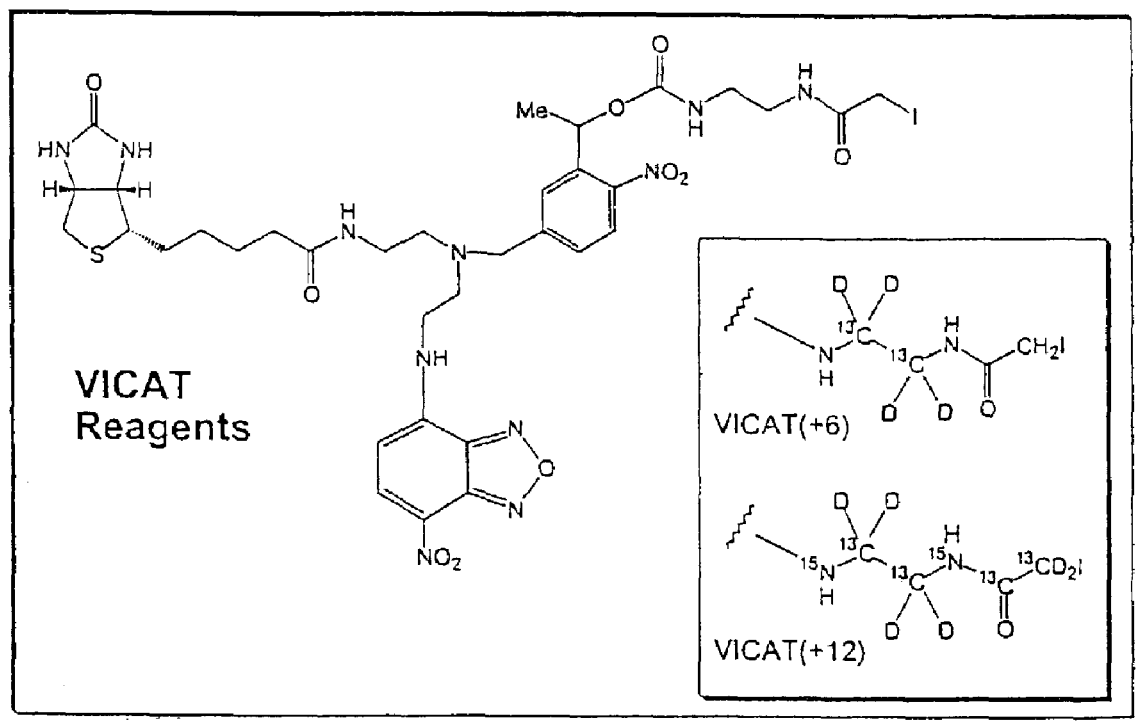
FIG. 1A shows the structure and synthetic scheme of a VICAT reagent having 7-nitrobenz-2-oxa-1,3-diazole (NBD) as the detectable moiety.

The invention provides reagents and methods for the detection of specific proteins in a complex sample. The methods can be used to quantify the amount of protein in the sample. The method is based on the concurrent introduction of a detectable moiety, for example, a fluorescent reagent or a radiolabel, a stable isotope tag, and an affinity tag at specific sites in a protein. The detectable moiety is used for the visualization of tagged peptides after proteolysis of the tagged protein sample and peptide separation. The stable isotope tag is used for accurate quantification of the abundance of the protein in the sample using a mass spectrometer. The affinity tag is required for the isolation of the tagged peptides. The reagent having these properties is termed VICAT, for Visible Isotope-coded Affinity Tag. To avoid complications in analyzing tandem mass spectra of tagged peptides caused by the relatively large VICAT group, the reagents can contain a cleavable linker for the removal of a major portion of the VICAT group prior to mass spectrometric analysis. The reagents and methods of the invention allow the rapid, sensitive and quantitative detection, as well as accurate absolute quantification, of selected proteins contained in complex samples.

A VICAT reagent of the invention has the following general structure: i) a functional group that specifically reacts with a chemical group in the target molecule, which is typically a protein; ii) a stable isotope tag that remains covalently attached to the specific target molecule and peptides derived from the target molecule; iii) a cleavable linker peripheral to the isotope tag; iv) a detectable group; and v) an affinity group.

The methods of the invention advantageously allow the detection of one or several selected proteins in complex samples and determination of their absolute quantity. In general, the method is based on the generation of labeled peptide standards for each target protein, where the peptide standards are chemically identical to, but isotopically distinguished from, the VICAT labeled peptides generated by enzymatic digestion of a protein sample mixture containing the target protein. The standard peptides are generated by chemical synthesis of the target peptide followed by labeling of the peptide with one isotopic form of the VICAT reagent. The standard peptides conjugated with a VICAT reagent are purified and can be quantitatively calibrated for use as a known standard.

Defined amounts of the labeled peptide standards are added to the protease digest of the sample, and the peptide mixture is separated by isoelectric focusing (IEF) in a polyacrylamide gel or in solution, for example, in a capillary. Other types of peptide separation can also be used, for example, reverse phase high pressure liquid chromatography (HPLC) or other well known methods of peptide separation, as disclosed herein. The location of the tagged peptides in the gel or capillary or other form of peptide separation is determined by fluorescence or visual imaging of a similarly prepared isoelectric focusing strip or capillary that contains only the VICAT-tagged peptide standards, or by autoradioagraphy or counting of radioactive fractions of the gel or capillary if the detectable moiety of the VICAT reagent is a radiolabel. The region of the sample-containing strip where the tagged peptides are located is extracted, and the tagged peptides are immobilized to affinity isolate the tagged peptides. The peptides are affinity isolated by contacting the tagged peptides with a solid support containing the cognate binding molecule of the affinity group of the VICAT reagent, for example, using avidin or streptavidin to bind to biotin on the VICAT reagent. Immobilized peptides are recovered either by adding a competitive ligand for the affinity group of the VICAT reagent, by changing the solution conditions such that the VICAT-peptide conjugate is released from the solid support, for example, by changing pH, salt, chaotropic agents, and the like, or by cleavage of a cleavable linker, leaving the isotope tag covalently attached to the peptide. The recovered peptides can be analyzed by mass spectrometry and, if required, by tandem mass spectrometry. Accurate protein quantification is achieved by calculating the ratio of signal intensities of the standard peptide and the differentially labeled peptide of identical sequence generated by enzymatic digestion of the protein sample.

Although described above with the affinity isolation step performed after a previous purification step, it is understood that the affinity isolation step of VICAT-labeled polypeptides can be performed at any convenient step of the methods of the invention. For example, the affinity isolation step can be performed prior to resolution on an IEF gel or chromatographic separation. Furthermore, the affinity isolation step can be performed prior to digestion with a protease, if desired. One skilled in the art can readily determine a suitable order for carrying out steps of the methods of the invention so long as VICAT-labeled peptides are isolated.

The method of the invention involves the separation of the peptide mixtures generated by the digestion of the labeled protein samples. Among the multitude of mature peptide separation methods available, a particularly useful method is isoelectric focusing in polyacrylamide gels with immobilized pH gradients. This method is particularly useful for the following reasons: i) it is robust, relatively inexpensive, highly reproducible and easily multiplexed. IEF strips covering different pH ranges are commercially available; ii) the method has immense separation power and the pH gradient and therefore the range of maximal separation can be tuned; iii) the pI of peptides can be reasonably accurately calculated from the amino acid sequence. The position of a specific target peptide in the gel can therefore be predicted; and iv) peptide recovery is simple and efficient.

The methods of the invention can be advantageously used for the detection and accurate absolute quantification for one or more particular proteins in a complex protein sample. The methods for detecting and quantitating proteins or other molecules in a sample can be used for a variety of purposes. For example, the methods of the invention can be used for the detection and quantification of proteins coded for by genetic disease genes in cell lysates or other protein extracts prepared from biopsies or body fluids for the purpose of diagnosis or prognosis. The methods of the invention are also useful for the detection and quantification of specifically modified forms of a protein. In addition, the methods of the invention can be used for the detection and quantification of sequence variants of a protein, including polymorphisms, splice isoforms and sequence variants created by post-translational processing. Furthermore, the methods of the invention can be used for the detection of a single or multiple marker proteins in a biological sample, including those that are diagnostic or prognostic for a specific disease. The methods of the invention are advantageous in allowing quantification of the absolute amounts of multiple proteins in a complex sample without the need for specific reagents such as antibodies and can be carried out within a simplified operation.

Moreover, because the methods can be used quantitatively, the methods of the invention can be used for the detection of changes in abundance of specific proteins in complex mixtures. For example, the detection of proteins that are aberrantly expressed in disease states, genetic or otherwise, that is, the detection of marker proteins, is common in clinical testing and diagnosis. Commonly, such tests are based on some form of immunodetection, for example, western blotting, ELISA, of the target protein(s), which requires one or several antibodies specific for the target protein, and typically one protein is measured per assay. In contrast, the methods of the invention are advantageous in that they allow the detection of changes in the abundance of a selected single protein or constellations of multiple proteins in complex samples.

The methods of the invention incorporate a modification of the previously described ICAT-based proteomics technology (Gygi et al., Nat. Biotechnol. 17:994-999 (1999); WO 00/11208, each of which is incorporated herein by reference). The use of an ICAT-type reagent is advantageous for detecting one or several proteins of known identity in a complex protein mixture and can be greatly simplified by the ability to readily prepare an internal standard that is chemically identical, but isotopically-distinguished, to the tagged peptides derived from the proteins of interest. The methods of the invention using a VICAT-type reagent advantageously allow the ready detection of the protein of interest using a detectable group such as a fluorophore or radiolabel. Thus, an ICAT-type reagent can be modified to contain a fluorophore, a visible dye, or radiolabel so that the internal standard can be readily detected and quantitatively calibrated either fluorimetrically or simply by eye in the case of colored fluorophores or dyes, or by autoradiography, liquid scintiallation counting or Cerenkov counting in the case of radiolabels. Since the target proteins are generally characterized using high-resolution chromatographic separation of peptides prior to their detection by ESI-MS, the reagents of the invention allow the chromatographic position of the tagged peptides of interests to be readily visualized.

Thus, Visible ICAT reagents (VICAT reagents) are prepared having the properties of an ICAT reagent (Gygi et al., supra, 1999; WO 00/11208). The VICAT-type reagent also contains a detectable moiety such as a fluorophore or radiolabel. A VICAT-type reagent also can include a cleavable linker. The inclusion of a cleavable linker allows release of a significant portion of the VICAT reagent after chromatographic separation and visualization of the VICAT-tagged protein of interest. After cleavage, a small, isotopically substituted fragment of the VICAT reagent remains covalently attached to the protein or peptide of interest. This allows the peptide from which the bulk of the VICAT reagent has been removed to be analyzed by tandem ESI-MS with the ion fragmentation directed in the peptide rather than in the tag. Peptide-directed fragmentation allows for peptide sequencing and thus peptide identification.

The reagents and methods of the invention have widespread application in quantitative biochemistry and proteomics. Among the advantages of the methods of the invention are the potential ability to detect and quantify multiple peptides in the same analysis (multiplexing), very precise quantification, and the lack of need for peptide-specific antibodies or other reagents.

The invention provides a VICAT reagent comprising an affinity tag, a detectable moiety, such as a fluorescent or non-fluorescent dye or radiolabel, a linker, which can be cleavable, a stable isotope tag, and a reactive group. The VICAT reagent is used to tag a molecule such as a polypeptide to modify the molecule with specific functionalities. In particular, the reactive group is a chemical moiety having reactivity for a chemical moiety on the target molecule. Thus, the reactive group couples the VICAT reagent to a target molecule. Once tagged with a VICAT reagent, the target molecule is attached to an affinity tag, a detectable moiety, a linker and an isotope tag. The affinity tag can be used to specifically isolate tagged molecules. The detectable group is used to visualize or locate tagged molecules. The linker serves to bridge the affinity tag and detectable group to the isotope tag. The linker can include a cleavable moiety so that the tagged molecule can be released from the affinity tag and detectable moiety. For example, if the affinity tag is used to affinity isolate tagged molecules on a solid support, the linker can be cleaved to release the affinity isolated tagged molecules.

The isotope tag is a chemical moiety that can be used to incorporate heavy isotopes, allowing the generation of multiple forms of a chemically identical but isotopically distinct moiety. Differential isotope tags are particularly useful for quantitative analysis since a sample molecule can be compared directly to a standard molecule, with the only difference being the differential isotope tag, thus allowing direct comparison between the sample and standard molecule. Due to the relative position of the functionalities of a VICAT reagent of the invention, the VICAT reagent can be used to affinity isolate peptides and release the peptides from the affinity support while concurrently transferring an isotope tag to the released peptides. Incorporation of the isotope tag allows comparison to standard peptides labeled with a differentially labeled isotope tag for convenient qualitative and/or quantitative analysis.

An exemplary VICAT reagent of the invention can have the general formula:

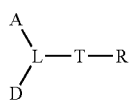

where A is an affinity tag, D is a detectable moiety, such as a fluorescent dye or radiolabel, L is a linker, which can be cleavable, T is an isotope tag, and R is a reactive group having a chemical functionality suitable for covalently coupling to a target molecule such as a protein. The formula above is representative of the VICAT reagents shown in FIGS. 1, 2 and 4. It is understood that any arrangement of the functionalities of the VICAT reagent can be employed so long as each of the moieties can function as disclosed herein and needed for a particular application. Generally, the affinity tag and detectable moiety are positioned so that the linker separates them from the isotope tag and reactive group, allowing cleavage of the affinity tag and detectable moiety from a tagged molecule. Thus, in addition to the formula shown above, a reagent of the invention can have the formula A-D-L-T-R or D-A-L-T-R, or any arrangement that allows the affinity tag, detectable moiety, linker, isotope tag, and reactive group to function as desired.

Figure 1B:
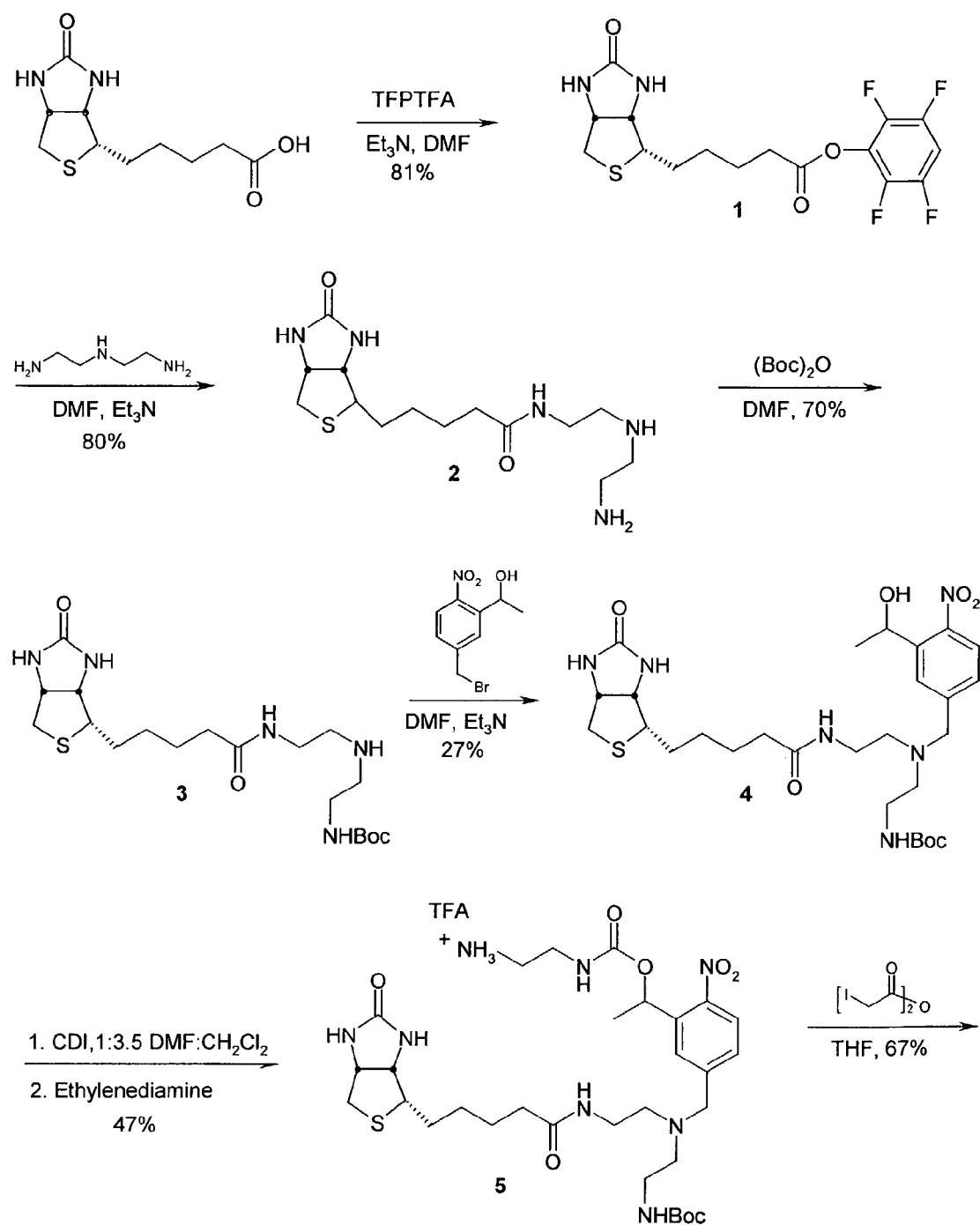
FIG. 1B shows a detailed reaction scheme for the synthesis-of a VICAT reagent having NBD as the detectable moiety. The structures of intermediate compounds 1-7 and final product, compound 8 (VICAT having NBD as detectable moiety), are shown.
Figure 1B:
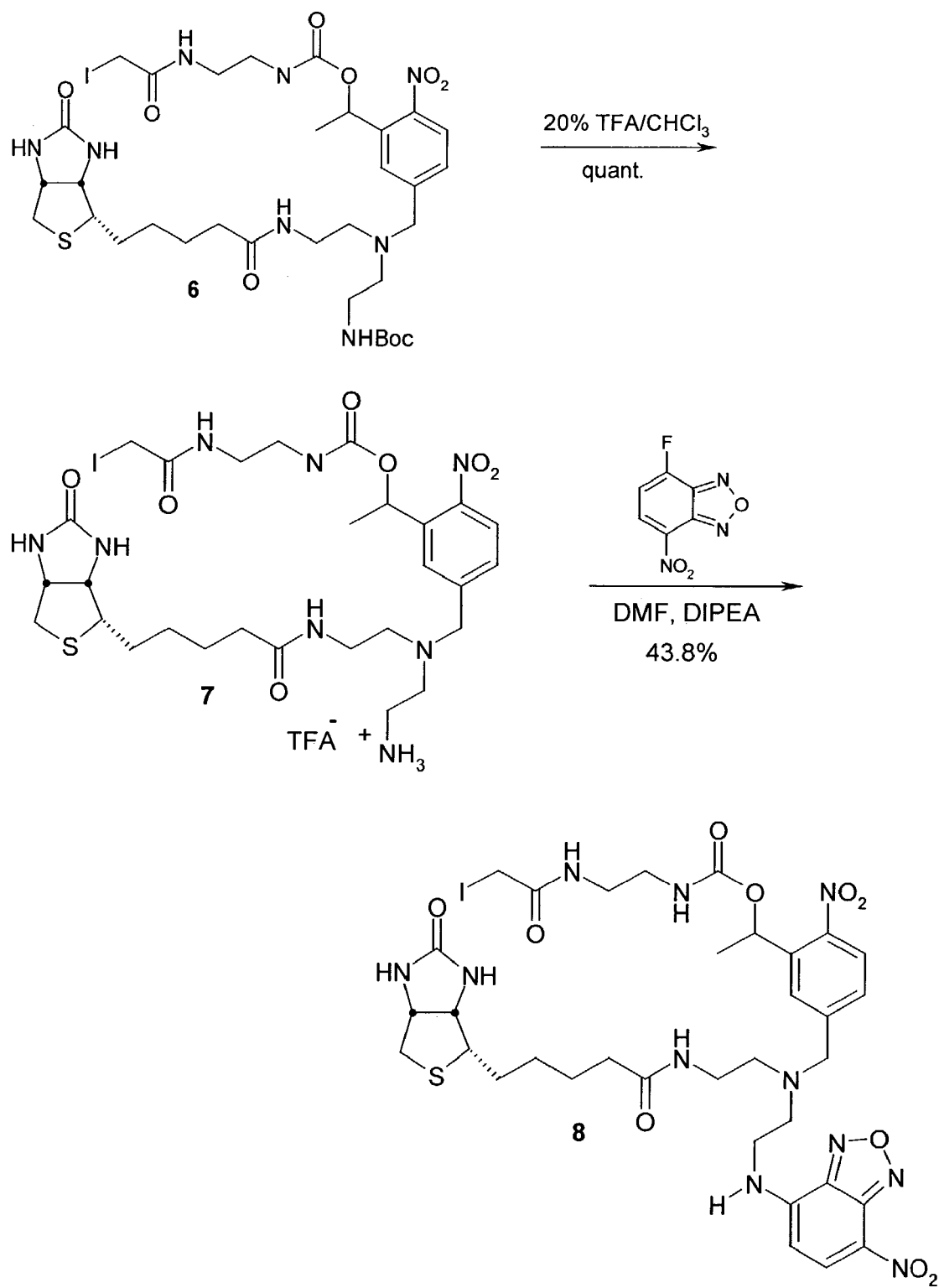
Figure 2:
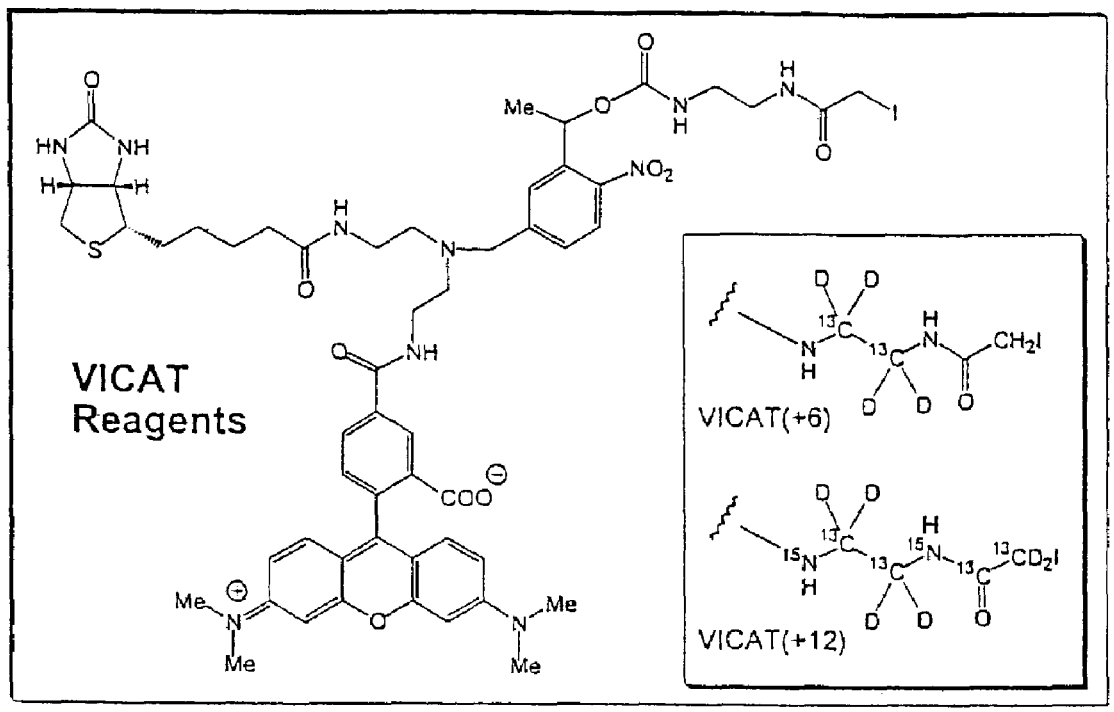
FIG. 2 shows the structure and synthetic scheme of a VICAT reagent having tetramethyl-rhodamine as the detectable moiety.
Figure 3:
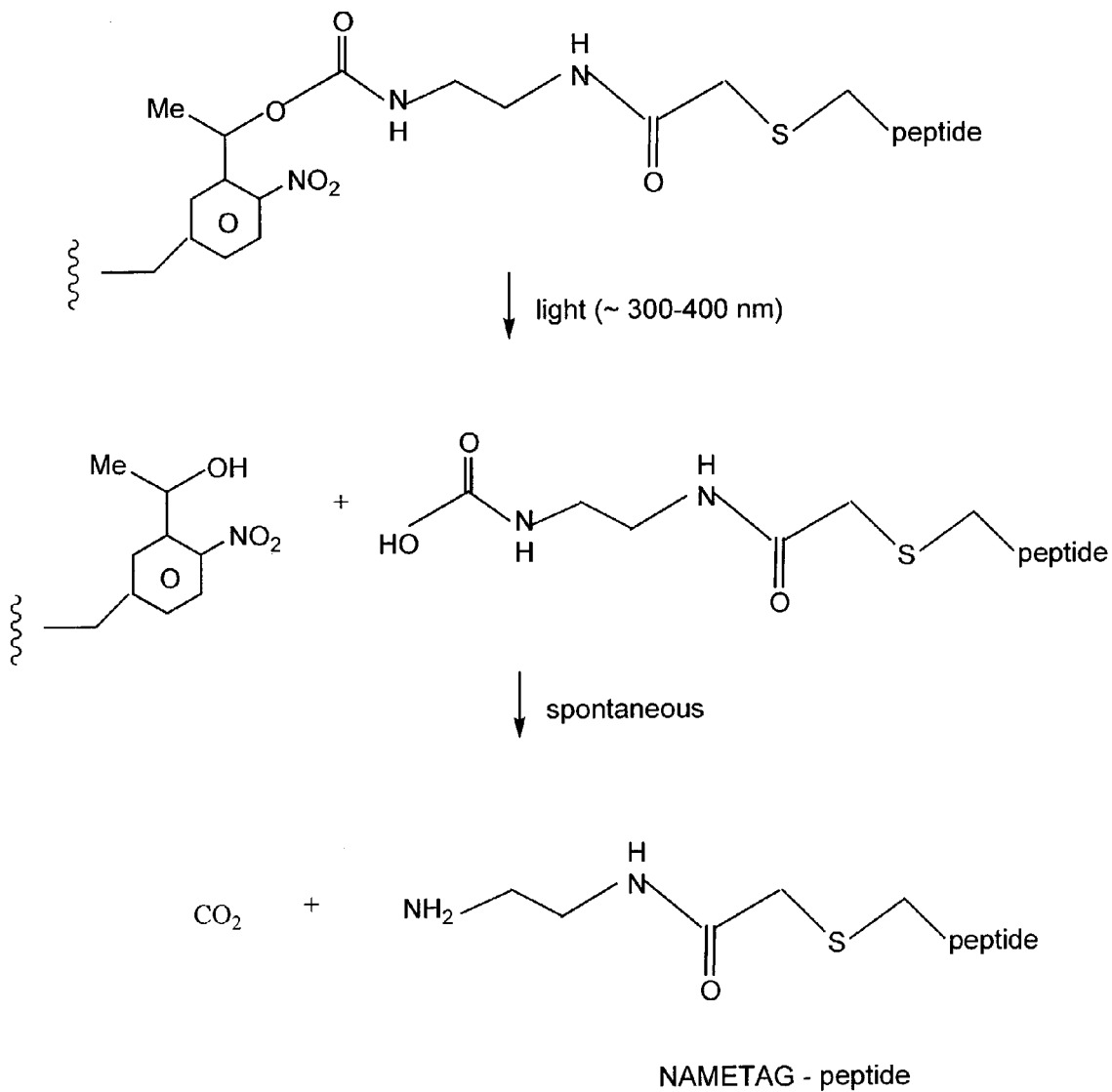
FIG. 3 shows photocleavage of a VICAT reagent-peptide conjugate. A portion of a VICAT reagent depicted in FIG. 2 is shown conjugated to a peptide. The VICAT-peptide conjugate undergoes photocleavage to generate a VICAT fragment and a peptide intermediate. The peptide intermediate spontaneously gives of $CO_2$ gas, yielding a NAMETAG-peptide conjugate as the final product. The NAMETAG portion can contain heavy isotopic substitution, as exemplified in FIG. 2.
Figure 4A:
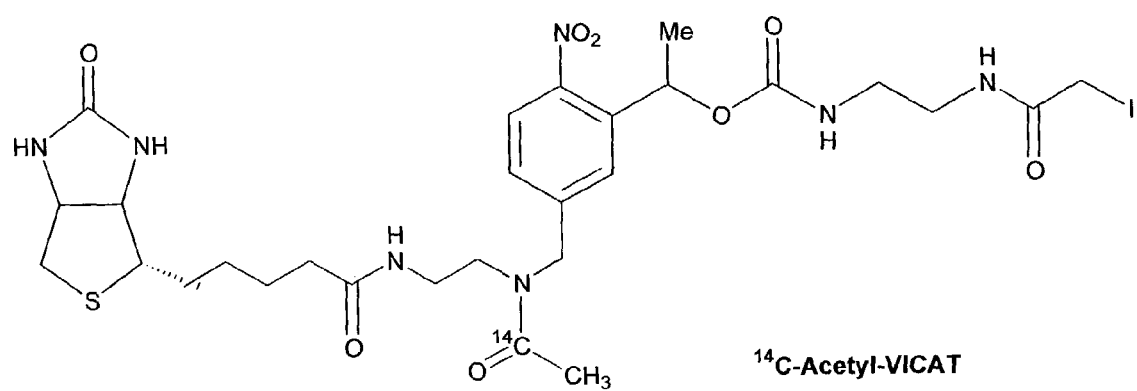
FIG. 4A shows the structure of a VICAT reagent having a radioactive acetyl group as the detectable moiety ($^{14}$C-Acetyl-VICAT).

The structures and synthetic schemes of exemplary VICAT reagents are shown in FIGS. 1, 2 and 4. The reactive functional group depicted in FIGS. 1, 2 and 4 is an iodoacetyl group, which specifically reacts with SH groups on reduced proteins. The particular isotope tag group depicted is an N-aminoethylacetamido group, also known as a NAMETAG group. The linker shown is a cleavable linker containing the photocleavable 2-(2-nitrophenyl)-ethan-2-ol group. The dye group shown in FIG. 1 is 7- nitrobenz-2-oxa-1,3-diazole (NBD). The dye group shown in FIG. 2 is 5-carboxytetramethylrhodamine. The affinity group shown is a biotin. FIG. 3 shows how the NAMETAG-peptide is formed after photocleavage of a VICAT-peptide conjugate.

The VICAT reagents described above and depicted in FIGS. 1, 2 and 4 are merely exemplary of the reagent of the invention having an affinity tag, a detectable moiety, a linker, and isotope tag, and a reactive group, which can have the general formulas described above. One skilled in the art will readily recognize that many structural variations of the structures shown in FIGS. 1, 2 and 4 would be suitable for a reagent of the invention and would provide the above-described characteristics.

In particular, an affinity tag of the VICAT reagent is used so that, when the VICAT reagent is attached to a molecule, the affinity tag can be used to isolate the molecule from a complex mixture. As used herein, an "affinity tag" refers to a chemical moiety having binding activity for a capture moiety. One skilled in the art can readily determine a suitable affinity tag for use in a VICAT reagent of the invention. The general features of an affinity tag include being stable, relatively small, having high affinity and specific binding activity to a cognate binding partner, being unlikely to undergo non-specific interactions and adsorption to vessels, and being soluble in aqueous solution. Accordingly, suitable criteria for selection of an affinity tag include but are not limited to a desired size, solubility, affinity and/or specificity for a particular capture moiety, lack of non-specific binding, the nature of the molecule to be captured, such as whether any of the sample molecules would be able to bind to the capture moiety, and the like. Any of these or other desirable criteria can be considered by one skilled in the art for affinity tag to be incorporated into a VICAT reagent of the invention. An exemplary affinity tag is biotin, and the corresponding capture moiety is avidin or streptavidin. Biotin is particularly useful as an affinity tag because it forms a high affinity interaction with avidin or streptavidin and can therefore readily be used to affinity isolate molecules that have reacted with the VICAT reagent.

In addition to biotin, other affinity tags can be used (see WO 00/11208). For example, modified biotin-based reagents can be used, including d-iminobiotin, which bind to avidin/streptavidin. Another useful biotin-based reagent is N-biotinyl-sarcosine, which binds tightly to avidin/streptavidin but can be released more easily than biotin (see Gerber et al., *Bioconj. Chem.* 12:603-615 (2001)). Maltose can also be used as an affinity tag since it binds to maltose binding protein. Similarly, other sugars and sugar binding molecules such as lectins are suitable as an affinity tag/capture moiety pair. Another suitable affinity tag/capture moiety pair includes glutathione, which binds to glutathione-S-transferase. In addition, a poly-His tag, generally containing about 5 to about 10 histidines, can be used to affinity purify a molecule using metal chelate chromatography.

Other suitable affinity tags include an epitope for which a specific antibody is available. An epitope can be, for example, a short peptide of about 3-5 amino acids or more, a carbohydrate, a small organic molecule, and the like. Epitope tags have been used to affinity purify recombinant proteins and are commercially available. For example, antibodies to epitope tags, including myc, FLAG, hemaglutinin (HA), green fluorescent protein (GFP), polyHis, and the like, are commercially available (see, for example, Sigma, St. Louis Mo.; PerkinElmer Life Sciences, Boston Mass.). In addition, a hapten, such as a dinitrophenyl group, can be used with an antibody specific for the hapten. Methods for making antibodies against an epitope tag are well known to those skilled in the art (Harlow and Lane, *Antibodies: A Laboratory Manual*, Cold Spring Harbor Laboratory Press (1988)). One skilled in the art can readily determine suitable affinity tags for isolation of molecules to which the VICAT reagent has been attached.

Yet another suitable affinity tag is a 1,2-diol, such as 1,2-dihydroxyalkanes, including those of cyclic alkanes, for example, 1,2-dihydroxycyclohexane, which bind to an alkyl or aryl boronic acid or boronic acid esters, such as phenyl-B(OH)$_2$ or hexyl-B(OEthyl)$_2$, which can be attached via the alkyl or aryl group to a solid support material, such as agarose. A nitrilotriacetic acid group can also be used as an affinity tag (WO 00/11208).

The above-described affinity tags can interact non-covalently with the corresponding capture moiety. Alternatively, an affinity tag can interact covalently with a capture moiety. In such a case, either the affinity tag or the capture moiety, in addition to containing chemical characteristics providing a specific interaction, contains a reactive group capable of reacting covalently to join the affinity tag and capture moiety. Such a covalent interaction would allow stringent wash conditions, and the presence of a cleavable linker in the VICAT reagent would allow release and tagging of the VICAT-labeled molecule(s), as disclosed herein.

Furthermore, it is understood that the affinity tag of the VICAT reagent need not be distinct from other moieties. If a capture moiety is available for another moiety of a VICAT reagent, then one moiety of the VICAT reagent can serve two functions. For example, antibodies are available against the detectable moiety fluorescein, and fluorescein can thus function as both an affinity tag and detectable moiety. Similarly, other moieties can have multiple functions in a VICAT reagent so long as each of the functions can work independently.

The VICAT-type reagents of the invention also include a detectable moiety. As used herein, a "detectable moiety" refers to a moiety that imparts a physicochemical property such that the moiety can be detected. Such a detectable moiety allows a VICAT-tagged molecule to be visualized. The detectable moiety is generally a moiety that allows convenient detection of the tagged molecule, for example, a fluorescent, a colored, or a calorimetric moiety. Similar to the desired characteristics of an affinity tag, the detectable moiety is generally stable, relatively small, is unlikely to undergo non-specific interactions and adsorption to vessels, and is soluble in aqueous solution. In the case of a fluorescent moiety, it is particularly useful for the moiety to have high quantum yield, a high absorption coefficient, and a quantum yield that is not solvent dependent. Accordingly, suitable criteria for selection of a detectable moiety include but are not limited to a desired size, solubility, lack of non-specific binding, desired method of detection including speed and convenience of detection, and the like. In the case of fluorescent detectable moieties, the criteria can include quantum yield and properties related to solvent, absorption coefficient, excitation and emission wavelengths, fluorescence lifetime, and the like. Any of these or other desirable criteria can be considered by one skilled in the art for affinity tag to be incorporated into a VICAT reagent of the invention.

Thus, the detectable group can be a fluorophore, such as rhodamine-type fluorophore depicted in FIG. 2. Other suitable fluorescent moieties are well known to those skilled in the art (see Hermanson, *Bioconjugate Techniques*, pp. 297-364, Academic Press, San Diego (1996); Molecular Probes, Eugene Oreg.). Rhodamine derivatives include, for example, tetramethylrhodamine, rhodamine B, rhodamine 6G, sulforhodamine B, Texas Red (sulforhodamine 101), rhodamine 110, and derivatives thereof such as tetramethylrhodamine-5-(or 6), lissamine rhodamine B, and the like. Other suitable fluors for a VICAT reagent include 7-nitrobenz-2-oxa-1,3-diazole (NBD)(see FIG. 1).

Additional exemplary fluorophores include, for example, fluorescein and derivatives thereof. Other flurophores include napthalenes such as dansyl (5-dimethylaminonapthalene-1-sulfonyl). Additional fluorophores include coumarin derivatives such as 7-amino-4-methylcoumarin-3-acetic acid (AMCA), 7-diethylamino-3-[(4'-(iodoacetyl)amino)phenyl]-4-methylcoumarin (DCIA), Alexa fluor dyes (Molecular Probes), and the like.

Other fluorophores include 4,4-difluoro-4-bora-3a,4a-diaza-s-indacene (BODIPY™) and derivatives thereof (Molecular Probes; Eugene Oreg.). Further fluorophores include pyrenes and sulfonated pyrenes such as Cascade Blue™ and derivatives thereof, including 8-methoxypyrene-1,3,6-trisulfonic acid, and the like. Additional fluorophores include pyridyloxazole derivatives and dapoxyl derivatives (Molecular Probes). Additional fluorophores include Lucifer Yellow (3,6-disulfonate-4-amino-naphthalimide) and derivatives thereof. CyDye™ fluorescent dyes (Amersham Pharmacia Biotech; Piscataway N.J.) can also be used.

In general, the detectable moiety is a relatively small organic molecule such as the fluorophores described above. However, it is understood that fluorescent proteins can also be used so long as the size of the fluorescent protein does not interfere with the other functions of the VICAT reagent or the needs of the particular experiment. Thus, other fluorescent moieties include phycobiliproteins and derivatives such as phycoerythrin and phycocyanin from various species, as well as green fluorescent protein and derivatives thereof or other fluorescent proteins.

The detectable moiety can also be a chromophore. Exemplary chromophores include, for example, phenolphthalein, malachite green, nitroaromatics such as nitrophenyl, diazo dyes, dabsyl (4-dimethylaminoazobenzene-4'-sulfonyl), and the like (see Hermanson, supra, 1996).

Although the detectable moiety is described above as a group that allows ready visualization of the VICAT-tagged molecule, it is understood that any moiety that imparts a detectable property can be used as a detectable moiety. Thus, a detectable moiety can be a radioactive moiety, which can be visualized by autoradiography, fluorography or phosphorimaging, or can be detected by scintillation or Cerenkov counting of chromatographic fractions, polyacrylamide gel or gel slices, or extracts of regions of a polyacrylamide gel. Suitable radioactive isotopes for use in a detectable moiety include, for example, $^{3}$H, $^{14}$C, $^{32}$P, $^{35}$S, $^{125}$I, and the like. Thus, a radioactive detectable moiety can include a chemical group that contains hydrogen, carbon, phosphorus, sulfur, iodine, and the like incorporated as a radioactive isotope. In addition, the detectable moiety can be chemiluminescent, can contain spin labels, can be detectable with ultraviolet light, or can be other detectable groups.

It is understood that, when a detectable moiety is a small moiety such as a radioactive atom, the detectable moiety can be incorporated into one of the other functional groups of a VICAT reagent. For example, a radioactive moiety can be attached to a linker as a separate chemical moiety or can be incorporated into the linker by using a radioactive atom in the linker. Similarly, one or more radioactive atoms can be incorporated into the affinity tag, isotope tag or reactive group. In such a case, the detectable moiety can be positioned so that it is removed upon cleavage of the linker. However, since the detectable moiety is relatively small, it can be positioned so that the detectable moiety is retained on the labeled polypeptide after cleavage of the linker and release from an affinity capture reagent. An exemplary radioactive VICAT reagent is depicted in FIG. 4.

The "linker" of a VICAT reagent is used to bridge the affinity tag and detectable moiety to the isotope tag and reactive group. The linker is generally a cleavable group. A cleavable group is particularly useful when mass spectrometry (MS) is being used as an analytical method. Because the affinity tag and detectable tag can be large moieties, it is useful to have the option of cleaving off these large groups from the molecules to be analyzed by MS. However, it is understood that cleavage of a cleavable linker or the use of a cleavable linker is not required so long as the groups of the VICAT reagent retained on the tagged molecule are compatible with the analytical method being used. Any of a number of chemical groups can be used to bridge the affinity tag and detectable moiety with the isotope tag and reactive group. Suitable criteria for selection of a linker include but are not limited to a desired size, solubility, ability to cleave or not cleave the linker, the type of cleavage method to be used, and the like. Any of these or other desirable criteria can be considered by one skilled in the art for affinity tag to be incorporated into a VICAT reagent of the invention.

A cleavable linker can be a photocleavable or chemically cleavable moiety. The photocleavable linker 2-(2-nitrophenyl)-ethan-2-ol is depicted in FIGS. 1, 2 and 4. Other suitable photocleavable linkers include, for example, linkers containing o-nitrobenzyl, desyl, trans-o-cinnamoyl, m-nitrophenyl, benzylsulfonyl groups (see, for example, Dorman and Prestwich, *Trends Biotech.* 18:64-77 (2000); Greene and Wuts, *Protective Groups in Organic Synthesis*, 2nd ed., John Wiley & Sons, New York (1991); U.S. Pat. Nos. 5,143,854; 5,986,076; 5,917,016; 5,489,678; 5,405,783). One skilled in the art will readily recognize that these exemplary photocleavable groups as well as others can be used in a VICAT reagent.

In addition to a photocleavable linker, a chemically cleavable linker can also be used. Exemplary cleavable linkers can contain a disulfide, which can be cleaved with reducing agents; a diol, which can be cleaved with periodate; a diazo bond, which can be cleaved with dithionate; an ester, which can be cleaved with hydroxylamine; and a sulfone, which can be cleaved with base (see Hermanson, *Bioconjugate Techniques*, Academic Press, San Diego (1996); Pierce Chemical Co., Rockford Ill.).

Furthermore, a linker cleavable by an enzyme can be used. For example, a protease can be used to cleave a cleavable linker having a suitable recognition sequence for the protease. Particularly useful proteases are endopeptidases such as factor Xa, tobacco etch virus (TEV) protease, trypsin, chymotrypsin, *Staphylococcus aureus* protease, submaxillaris protease, and the like. The protease can be selected based on the incorporation of a particular cleavable recognition sequence into the linker. Other considerations for selecting a protease include the presence or absence of a recognition sequence in the molecule being captured and released.

For example, a rare cleaving protease such as TEV protease or factor Xa can be used to cleave a functional group containing the corresponding protease recognition sequence, resulting in release of the captured molecule. Such rare cleaving proteases are particularly useful for releasing an intact polypeptide molecule since the recognition sequence for these proteases would not occur in the vast majority of polypeptides. Alternatively, a polypeptide sample can be treated with a specific protease, and the digested peptides isolated by the methods disclosed herein. In such a case, the captured peptides would not contain a recognition sequence for the protease used for cleavage since the polypeptide has already been digested. In addition, if desired, an intact polypeptide can be captured and digested with a protease after binding to the solid support, resulting in the incorporation and release of a label on the peptide fragment of the polypeptide that was captured on the solid support. Thus, protease digestion can be used before or after capture of a sample molecule, as desired.

In addition to proteases, a cleavable functional group can be a recognition sequence for an endonuclease such as a restriction enzyme. Thus, an appropriate recognition sequence for a restriction enzyme can be incorporated as a cleavable functional group and cleaved with the respective restriction enzyme. It is understood that such a nucleotide functional group can be useful for capturing and releasing a nucleic acid or a polypeptide, or any other type of molecule, as desired. Similarly, a protease recognition sequence can be useful for capturing and releasing a polypeptide, nucleic acid or any other type of molecule, as desired.

A VICAT reagent of the invention also contains a stable isotope tag. As used herein an "stable isotope tag" refers to a chemical moiety having suitable chemical properties for incorporation of a stable isotope, allowing the generation of differentially labeled reagents which can be used to differentially tag a polypeptide in two samples. The isotope tag, in combination with the linker, has a sufficient length to allow the reactive group to bind to a sample polypeptide and the affinity tag to bind to its cognate binding partner. The isotope tag also has an appropriate composition to allow incorporation of a stable isotope at one or more atoms. A particularly useful stable isotope pair is hydrogen and deuterium, which can be readily distinguished using mass spectrometry as light and heavy forms, respectively. Any of a number of isotopic atoms can be incorporated into the isotope tag so long as the heavy and light forms can be distinguished using mass spectrometry, for example, $^2H$, $^{13}C$, $^{15}N$, $^{17}O$, $^{18}O$ or $^{34}S$. Differential isotopic tags will generally differ by minimally 2 mass units and up to about 20 mass units, for example, about 4 to about 16 mass units, about 6 to about 12 mass units, and the like. Accordingly, the mass difference can be 2, 3, 4, 5, 6, 7, 8, 9, 10, 11, 12, 13, 14, 15, 16, 17, 18, 19 or 20 mass units, or even a greater number of mass units. One skilled in the art can readily determine an appropriate mass differential suitable for isotope tags for detecting mass differences of VICAT-labeled molecules using mass spectrometry. A multiple of a particular isotope can be incorporated and/or a combination of isotopes (see FIGS. 1 and 2).

Suitable criteria for selection of an affinity tag include but are not limited to a desired size, solubility, the presence of a suitable type and number of atoms for incorporation of desired heavy isotope(s) sufficient for MS analysis, and the like. Any of these or other desirable criteria can be considered by one skilled in the art for affinity tag to be incorporated into a VICAT reagent of the invention.

Exemplary isotope tags include the 4,7,10-trioxa-1,13-tridecanediamine based linker and its related deuterated form, 2,2',3,3',11,11',12,12'-octadeutero-4,7,10-trioxa-1,13-tridecanediamine, described by Gygi et al. (supra, 1999). Other exemplary isotope tags include a diethylenediamine, as shown in FIGS. 1, 2 and 4. One skilled in the art can readily determine any of a number of appropriate isotope tags useful in an VICAT-type affinity reagent that satisfy the above-described criteria. As used herein, the portion of the VICAT reagent which will remain attached to a sample molecule upon cleavage of a cleavable linker and which has sufficient chemical characteristics to allow the incorporation of isotopic atoms is considered to be an isotope tag. It is understood that such a portion is considered an isotope tag, regardless of whether different isotopes have been incorporated into the tag. Thus, as shown in FIGS. 1 and 2, three VICAT reagents are depicted that are differentially labeled in the isotope tag, one with no heavy isotope and the others depicted as +6 and +12 forms.

Thus, an isotope tag can be an alkyl, alkenyl, alkynyl, alkoxy, aryl, and the like; at least one of the carbons can be replaced with O, S, N; can contain O, S, NH, NR, NRR', CO, COO, COS, S—S, SO, $SO_2$, SH, CO—NR', CS—NR', Si—O, aryl or diaryl group, where R is an alkyl, alkenyl, alkynyl, alkoxy, or aryl group and R' is hydrogen, an alkyl, alkenyl, alkynyl, alkoxy or aryl group; and can be optionally substituted, for example, with O, S, N, and the like, and can contain an amine, carboxyl, sulfhydryl, and the like (see WO 00/11208). An isotope tag is generally of about 2 to about 100 atoms, although can be larger, for example, about 2 to about 50 atoms, about 2 to about 40 atoms, about 2 to about 30 atoms, about 2 to about 20 atoms, or about to 2 to about 10 atoms in length.

The above-described isotope tags and other derivatives can be made in the same manner as that disclosed herein using methods well known to those skilled in the art. One skilled in the art will readily recognize that a number of suitable chemical groups can be used as an isotope tag so long as the isotope tag can be differentially isotopically labeled. One skilled in the art can readily determine a number of suitable isotope tags of various sizes based on criteria such as desired size of the tag, chemical composition for incorporation of desired atom types and number of differential isotopes, convenience of chemical synthesis, chemical stability, and the like. The isotope tag has at least a minimal size that allows sufficient differential labeling of the isotope tag suitable for analysis in a mass spectrometer. For example, the isotope tag is selected so that a sufficient mass differential can be detected in a mass spectrometer, taking into account naturally occurring isotope distribution (mostly $^{13}C$) that can overlap with the isotope tagged molecules if the mass differential is small. One skilled in the art can readily recognize these and other desirable characteristics of an isotope tag.

The use of an isotope tag is particularly useful for quantifying the amount of sample molecules using mass spectrometry. The method is based on derivatizing a specimen molecule such as a polypeptide with a VICAT reagent. A control reference sample, for example, synthesized known proteins or peptides or a control sample, and a test sample are differentially labeled with lighter and heavier forms of the VICAT affinity reagent. For quantitative analysis, the derivatized samples can be combined and analyzed in parallel using mass spectrometry, as described below (see Gygi et al., supra, 1999).

A VICAT reagent of the invention also has a "reactive group," which is reactive with a chemical moiety on a molecule in a sample and therefore can be covalently coupled to a molecule in a sample such as a polypeptide. Reactive groups are well known to those skilled in the art (see, for example, Hermanson, supra, 1996; Glazer et al., *Laboratory Techniques in Biochemistry and Molecular Biology: Chemical Modification of Proteins,* Chapter 3, pp. 68-120, Elsevier Biomedical Press, New York (1975); Pierce Catalog, Pierce, Rockford Ill.). Any of a variety of reactive groups can be incorporated into a VICAT type affinity reagent so long as the reactive group can be covalently coupled to a polypeptide or other desired molecule in a sample. The reactive group can also be a group that reacts with a moiety on a target sample molecule in the presence of an extrinsic reagent such as a crosslinking reagent. For example, bis-maleimide can be used to crosslink an SH group on a peptide with an SH group on the VICAT reagent. These and other cross-linking reagents suitable for coupling a peptide to a VICAT reagent are well know to those skilled in the art (see, for example, Hermanson, supra, 1996; Glazer et al., supra, 1975; Pierce).

Suitable criteria for selection of a reactive group include but are not limited to the type of molecule to be targeted with the VICAT reagent, the particular chemical moiety on the target molecule to be reacted, the stability of the reactive group under the buffer conditions used for the reaction, and the like. Any of these or other desirable criteria can be considered by one skilled in the art for affinity tag to be incorporated into a VICAT reagent of the invention.

For example, a polypeptide can be coupled to the ICAT type affinity reagent via a sulfhydryl reactive group, which can react with free sulfhydryls of cysteine or reduced cystines in a polypeptide. An exemplary sulfhydryl reactive group includes an iodoacetamido group (see Gygi et al., supra, 1999). Other exemplary sulfhydryl reactive groups include maleimides, alkyl and aryl halides, haloacetyls, α-haloacyls, pyridyl disulfides, aziridines, acrylolyls, arylating agents and thiomethylsulfones. If desired, the polypeptides can be reduced, for example, with tri-butylphosphine, dithiothreitol, mercaptoethanol, and the like, prior to reacting with a VICAT type reagent, which is particularly useful when the VICAT reagent contains a sulfhydryl reactive group.

A reactive group can also react with amines such as the α-amino group of a peptide or the ∈-amino group of the side chain of Lys, for example, imidoesters, N-hydroxysuccinimidyl esters (NHS), isothiocyanates, isocyanates, acyl azides, sulfonyl chlorides, aldehydes, ketones, glyoxals, epoxides (oxiranes), carbonates, arylating agents, carbodiimides, anhydrides, and the like. In addition, a vinyl sulfone such as R—$SO_2$—CH=$CH_2$ or R—$NHSO_2$—CH=$CH_2$, which can undergo a nucleophilic Michael-type addition reaction, can be used to react with sulfhydryl or amine groups on the target molecule.

A reactive group can also react with carboxyl groups found in Asp or Glu or the C-terminus of a peptide, for example, diazoalkanes, diazoacetyls, carbonyldiimidazole, carbodiimides, and the like. A reactive group that reacts with a hydroxyl group includes, for example, epoxides (oxiranes), carbonyldiimidazoles, N,N'-disuccinimidyl carbonates, N-hydroxycuccinimidyl chloroformates, and the like. A reactive group can also react with amino acids such as His, Tyr, Arg, and Met. In addition, a reactive group can also react with a phosphate group for selective labeling of phosphopeptides, or with other covalently modified peptides, including glycopeptides, lipopeptides, or any of the known covalent polypeptide modifications. One skilled in the art can readily determine conditions for modifying sample molecules by using various reagents, incubation conditions and time of incubation to obtain conditions optimal for modification of sample molecule for use in reagents and methods of the invention.

The reactive groups described above can form a covalent bond with the target sample molecule. However, it is understood that a VICAT reagent can contain a group that can non-covalently interact with a sample molecule so long as the interaction has high specificity and affinity.

A VICAT reagent of the invention can contain any combinations of the above-described affinity tags, detectable moieties, linkers, isotope tags, and reactive groups, as well as others well known to those skilled in the art. For example, a VICAT reagent can contain the affinity tag biotin, the detectable moiety rhodamine, the photolabile linker 2-nitrobenzyloxycarbonyl, the isotope tag ethylenediamine, and the reactive group iodacetyl, as depicted in FIG. 2. Another VICAT reagent can contain the affinity tag biotin, the detectable moiety 7-nitrobenz-2-oxa-1,3-diazole (NBD), the photolabile linker 2-nitrobenzyloxycarbonyl, the isotope tag ethylenediamine, and the reactive group iodacetyl, as depicted in FIG. 1. The reagent depicted in FIG. 1 is particularly useful because it is easy to make, is stable, and has solubility properties in aqueous solution sufficient for quantitative proteomics analysis. An additional VICAT reagent can contain the affinity tag biotin, the radioactive detectable moiety $^{14}C$-acetyl, the isotope tag ethylenediamine, and the reactive group iodacetyl, as depicted in FIG. 4.

Still another VICAT reagent can contain the affinity tag glutathione, the detectable moiety coumarin, a linker containing a benzylsulfonyl group, the isotope tag tridecanediamine, and an isothiocyanate reactive group. Yet another VICAT reagent can contain the affinity tag poly-His with six histidines, the detectable moiety BIDIPY, a linker containing a disulfide, the isotope tag dodecane, and a disuccinimidyl carbonate reactive group.

The above-described VICAT reagents are merely exemplary of the VICAT reagents that can be readily prepared by one skilled in the art in the same manner as that disclosed herein using well known methods of chemical synthesis, including methods similar to those exemplified herein (see Example I). Based on the desired application of the VICAT reagent, one skilled in the art can select a suitable affinity tag, detectable moiety, linker, isotope tag, and reactive group sufficient for desired criteria, as disclosed herein.

The VICAT reagents of the invention can be used to label molecules in a sample. The methods are particularly useful for labeling polypeptides in a sample, and can thus be used for qualitative and quantitative proteome analysis. Although labeling of polypeptides is exemplified herein, it is understood that sample molecule having chemical properties reactive with the VICAT reagent reactive group can be labeled with a VICAT reagent of the invention. For example, a VICAT reagent can be used to label nucleic acids, carbohydrates, lipids, metabolites or other sample molecules.

The invention also provides a method of isolating a polypeptide in a sample. The method can include the steps of contacting a sample with a VICAT reagent of the invention under conditions allowing the reactive group to bind to and react with one or more polypeptides in the sample, thereby tagging one or more polypeptides with the reagent; resolving the polypeptides in the sample; visualizing the polypeptides tagged with the reagent; contacting the tagged polypeptides with a capture moiety for the affinity tag; and isolating the tagged polypeptides. It is understood that the steps of this method and other methods of the invention can be performed in any order so long as a VICAT reagent tags a sample molecule and can be used to isolate a target molecule. For example, an affinity isolation step of a VICAT-labeled molecule can be performed before or after other fractionation steps used to resolve molecules in a sample and can be performed before or after a visualization step. Furthermore, a sample can be resolved using various fractionation methods prior to labeling with a VICAT reagent. One skilled in the art can readily determine an appropriate order for carrying out steps of the methods of the invention suitable for tagging and isolating a sample molecule.

As used herein, the term "polypeptide" refers to a peptide or polypeptide of two or more amino acids. A polypeptide can also be modified by naturally occurring modifications such as post-translational modifications, including phosphorylation, fatty acylation, prenylation, sulfation, hydroxylation, acetylation, addition of carbohydrate, addition of prosthetic groups or cofactors, formation of disulfide bonds, proteolysis, assembly into macromolecular complexes, and the like.

The invention provides a method of labeling a polypeptide in a sample by contacting a sample with a VICAT reagent of the invention under conditions allowing the reactive group to bind to one or more polypeptides in the sample. One skilled in the art can readily determine appropriate conditions so that the reactive group of a VICAT reagent can react with a sample molecule, including appropriate buffers, salts, pH, temperature, and the like (see Hermanson, supra, 1996). Thus, a VICAT reagent of the invention can be used to label a sample molecule via the reactive group, resulting in the attachment of the VICAT reagent and corresponding isotope tag to a sample molecule.

Once a VICAT reagent has reacted with a sample molecule, the sample is labeled in a manner that allows convenient visualization of the labeled molecule(s). For example, any of the visualization methods disclosed herein can be used to conveniently locate the labeled molecules. Such a visualization is particularly useful for locating a labeled sample molecule when a complex sample molecule has been resolved from other sample molecules. As used herein, "resolving" when used in reference to a sample molecule refers to using a purification or fractionation step that separates the sample molecule from at least one other molecule in the sample. Thus, the method can further include the step of visualizing the molecules tagged with the VICAT reagent.

As used herein, the term "sample" is intended to mean any biological fluid, cell, tissue, organ or portion thereof, that includes one or more different molecules such as nucleic acids, polypeptides, or small molecules. A sample can be a tissue section obtained by biopsy, or cells that are placed in or adapted to tissue culture. A sample can also be a biological fluid specimen such as blood, urine or saliva. A sample can additionally be a cell extract from any species, including prokaryotic and eukaryotic cells as well as viruses. A tissue sample can be further fractionated, if desired, to a fraction containing particular cell types.

Furthermore, the sample can be fractionated by a number of known fractionation techniques. Since such fractionation methods separate molecules, such techniques are used to resolve sample molecules. Methods for resolving sample molecules are well known to those skilled in the art. Fractionation methods, which can be used to resolve sample molecules, include but are not limited to subcellular fractionation or chromatographic techniques such as ion exchange, including strong and weak anion and cation exchange chromatography, hydrophobic and reverse phase, size exclusion, affinity, hydrophobic charge-induction chromatography, dye-binding, and the like (Ausubel et al., *Current Protocols in Molecular Biology* (Supplement 56), John Wiley & Sons, New York (2001); Scopes, *Protein Purification: Principles and Practice*, third edition, Springer-Verlag, New York (1993); Burton and Harding, *J. Chromatogr. A* 814:71-81 (1998)). Other fractionation methods include, for example, centrifugation, electrophoresis, the use of salts, and the like (see Scopes, supra, 1993).

Affinity chromatography can also be used including, for example, dye-binding resins such as Cibacron blue, substrate analogs, including analogs of cofactors such as ATP, NAD, and the like, ligands, specific antibodies useful for immunoaffinity isolation, either polyclonal or monoclonal, and the like. An exemplary affinity resin includes affinity resins that bind to specific moieties that can be incorporated into a polypeptide such as an avidin resin that binds to a biotin tag on a sample molecule labeled with a VICAT reagent of the invention, as disclosed herein. The resolution and capacity of particular chromatographic media are known in the art and can be determined by those skilled in the art. The usefulness of a particular chromatographic separation for a particular application can similarly be assessed by those skilled in the art.

Those of skill in the art will be able to determine the appropriate chromatography conditions for a particular sample size or composition and will know how to obtain reproducible results for chromatographic separations under defined buffer, column dimension, and flow rate conditions. The fractionation methods can optionally include the use of an internal standard for assessing the reproducibility of a particular chromatographic application or other fractionation method. Appropriate internal standards will vary depending on the chromatographic medium or the fractionation method used. Those skilled in the art will be able to determine an internal standard applicable to a method of fractionation such as chromatography.

Electrophoresis, including gel electrophoresis or capillary electrophoresis, can also be used to resolve sample molecules. As disclosed herein, isoelectric focusing (IEF) is a particularly useful method to resolve sample polypeptides. As discussed herein, sample molecules can be processed, for example, by protease cleavage into peptide fragments. Accordingly, when referring to sample molecules, the sample molecules can be intact as found in an original sample or can be processed, for example, into smaller molecules such as peptides from a polypeptide sample.

If desired, sample molecules can be modified, either before or after a fractionation step. For example, the methods of the invention are particularly useful for mass spectrometry (MS) analysis. In the case of MS analysis of polypeptides, it is often useful to cleave the polypeptide into smaller fragments, for example, by proteolysis. Thus, a polypeptide molecule can be enzymatically cleaved with one or more proteases into peptide fragments. Exemplary proteases useful for cleaving polypeptides include trypsin, chymotrypsin, pepsin, papain, *Staphylococcus aureus* (V8) protease, and the like. Polypeptides can also be cleaved chemically, for example, using CNBr, acid or other chemical reagents.

For polypeptide fragmentation, the polypeptides in the sample mixture, or the polypeptides contained in each fraction if optional sample fractionation is employed, can be subjected to sequence specific cleavage, such as cleavage by trypsin. The use of sequence specific cleavage can be particularly useful because the termini of peptides cleaved by a sequence specific method can act as a constraint. However, it is understood that the cleavage method used to generate fragments need not be sequence specific, if desired.

Furthermore, for polypeptide tagging, the polypeptides in the sample can be denatured and optionally reduced. Reducing the sample can be particularly useful when the reactive group on the VICAT reagent is reactive with a thiol. Other useful reactive groups include amino or carboxyl groups of polypeptides or specific post-translational modifications, including phosphate, carbohydrate or lipid.

The methods of the invention involve the coupling of a VICAT-type reagent to a sample molecule, which results in the incorporation of a visible tag, which is detectable as disclosed herein. Such a visible tag is particularly useful for visualizing the location of a sample molecule resolved by a fractionation method. Thus, in a complex sample, the visible tag allows the convenient localization of a VICAT-labeled molecule. Furthermore, as disclosed herein, a specific sample molecule can be identified by preparing known standards and running the standards in parallel or in the same sample to facilitate the visualization of a particular desired sample molecule. If the standard molecules are added to the sample molecules, a relatively high amount of the standard can be added to indicate the position of the corresponding target molecule of interest.

The ability to readily visualize a VICAT-labeled molecule facilitates further characterization of the labeled molecule, regardless of the complexity of the original sample. In a complex sample, it is likely that a number of sample molecules will be labeled by the reactive group of the VICAT reagent. For example, the methods of the invention are particularly useful for proteomics analysis, where the sample molecules to be analyzed are polypeptides or peptide fragments thereof. By running a sample in parallel with a known standard, a particular sample molecule can be readily visualized. A known sample molecule can be synthesized, labeled with a VICAT reagent, and run in parallel under essentially the same conditions as the sample molecules. For example, a known polypeptide can be synthesized, optionally added to an unlabeled sample, and resolved in the same manner as the VICAT-labeled sample. Since the samples molecules are run under similar conditions, the location of the known polypeptide, also tagged with the VICAT reagent, can readily be determined in the parallel sample. Alternatively, a known molecule can be synthesized and labeled with the same VICAT reagent, but having a different detectable moiety, and run together with the sample molecules. In such a case, the different detectable moiety would have essentially the same resolution as the other detectable moiety in the particular fractionation method used. An example of this is the use of a radiolabel as the detectable moiety. The radiolabeled standard is added to the sample, and the position of the analyte to be analyzed is detected by autoradiography, fluorimetry, phosphor storage imaging, or liquid scintillation or Cerenkov counting.

Furthermore, a VICAT-labeled standard molecule can be used to calibrate a particular separation method so that the position of a corresponding VICAT-labeled sample molecule can be predicted when run under substantially similar conditions. Because a separation method can be performed reproducibly when run under substantially similar conditions, a VICAT-labeled standard molecule can be run on a separation medium under defined conditions so that the location of the VICAT-labeled standard molecule can be used to predict the location of a VICAT-labeled sample molecule run under the same defined conditions. This obviates the need to add the standard molecule to the sample or to run the standard molecule in parallel. Such an approach can be particularly useful for analysis by IEF.

Once a VICAT-labeled molecule of interest has been visualized and located in the separation medium, the VICAT-labeled molecule can be isolated by contacting with a capture moiety corresponding to the affinity tag of the VICAT reagent. Alternatively, the VICAT-labeled molecule can be affinity isolated by the capture moiety prior to resolution on a separation medium or visualization. For example, if the sample molecules are resolved by IEF electrophoresis, the region containing the VICAT-labeled sample molecule of interest can be extracted and contacted with an appropriate capture moiety (see Example III). Thus, by visualizing the resolved sample molecules to locate a VICAT-labeled molecule, the VICAT-labeled molecule of interest can be further processed and affinity purified in the absence of other VICAT-labeled molecules.

The capture moiety can be attached, for example, to a bead, resin, membrane or disk, or can be coupled to any type of solid support suitable for the isolation of the VICAT-labeled molecule(s). It is understood that the affinity tag can bind to a capture moiety directly bound to the solid support or to a capture moiety that binds via a secondary agent to the solid support. For example, the capture moiety can be bound in solution to the VICAT-labeled molecule and subsequently bound to a solid support, such as by binding to an antibody specific for the capture moiety. One skilled in the art can readily determine a desired method to affinity isolate a VICAT-labeled molecule using well known affinity isolation methods.

The invention thus provides a method of isolating one or more polypeptides in a sample. The method can include the steps of contacting a sample with a VICAT reagent of the invention under conditions allowing the reactive group to bind to and react with one or more polypeptides in sample, thereby tagging one or more polypeptides with the reagent; resolving the polypeptides in the sample; visualizing the polypeptides tagged with the reagent; contacting the tagged polypeptides with a capture moiety for the affinity tag; and isolating the tagged polypeptides. In addition to labeling polypeptides, this and other methods of the invention can be used to label other types of sample molecules such as carbohydrates, nucleic acids, and the like, if desired. Since the linker of the VICAT reagent can be cleavable, the method can further include the step of cleaving the linker. The cleavage results in the release of the VICAT-labeled molecule such that the molecule retains the isotope tag but is separated from the detectable moiety and affinity tag. Thus, the VICAT-labeled molecules can be readily released from an affinity resin or other solid support to which the labeled molecules are bound.

The isolated VICAT-labeled molecules can be further characterized, if desired. A particularly useful method for characterizing sample molecules is mass spectrometry (MS), which can be used to identify and/or quantify the VICAT-labeled molecule. Thus, the invention provides a method of identifying a polypeptide in a sample. The method can include the steps of contacting a sample with a VICAT reagent of the invention under conditions allowing the reactive group to bind to and react with one or more polypeptides in the sample, thereby tagging one or more polypeptides with the reagent; resolving the polypeptides in the sample; visualizing the one or more polypeptides tagged with the reagent; contacting the one or more tagged polypeptides with a capture moiety for the affinity tag; isolating the one or more tagged polypeptides; cleaving the linker of the reagent to release the one or more tagged polypeptides; and identifying a released tagged polypeptide.

The invention additionally provides a method of identifying a polypeptide in a sample. The method can include the steps of contacting a sample with a VICAT reagent of the invention under conditions allowing the reactive group to bind to and react with one or more polypeptides in the sample, thereby labeling one or more polypeptides with the reagent; cleaving the polypeptides in the sample to generate peptide fragments; adding one or more peptide standards to the sample, wherein the peptide standards correspond to peptides generated from cleaving sample polypeptides and are labeled with an isotopically distinct version of the isotope tag; resolving the labeled peptides in the sample; visualizing the labeled peptides; contacting the labeled peptides with a capture moiety for the affinity tag; isolating the labeled peptides; cleaving the linker of the reagent to release the isolated peptides; and identifying a released peptide. The identifying and/or quantifying step can be performed using mass spectrometry or tandem mass spectrometry.

A variety of mass spectrometry systems can be employed in the methods of the invention for identifying and/or quantifying a sample molecule such as a polypeptide. Mass analyzers with high mass accuracy, high sensitivity and high resolution include, but are not limited to, matrix-assisted laser desorption time-of-flight (MALDI-TOF) mass spectrometers, electrospray ionization time-of-flight (ESI-TOF) mass spectrometers and Fourier transform ion cyclotron mass analyzers (FT-ICR-MS). Other modes of MS include ion trap and triple quadruple mass spectrometers. In ion trap MS, analytes are ionized by electrospray ionization or MALDI and then put into an ion trap. Trapped ions can then be separately analyzed by MS upon selective release from the ion trap. Fragments can also be generated in the ion trap and analyzed. Sample molecules such as polypeptides labeled with a VICAT type reagent can be analyzed, for example, by single stage mass spectrometry with a MALDI-TOF or ESI-TOF system. Methods of mass spectrometry analysis are well known to those skilled in the art (see, for example, Yates, *J. Mass Spect.* 33:1-19 (1998); Kinter and Sherman, *Protein Sequencing and Identification Using Tandem Mass Spectrometry,* John Wiley & Sons, New York (2000); Aebersold and Goodlett,. *Chem. Rev.* 101:269-295 (2001); Griffin et al., *Curr. Opin. Biotechnol.* 12:607-612 (2001)).

For high resolution polypeptide fragment separation, liquid chromatography ESI-MS/MS or automated LC-MS/MS, which utilizes capillary reverse phase chromatography as the separation method, can be used (Yates et al., *Methods Mol. Biol.* 112:553-569 (1999)). Data dependent collision-induced dissociation (CID) with dynamic exclusion can also be used as the mass spectrometric method(Goodlett, et al., *Anal. Chem.* 72:1112-1118 (2000)).

Differentially labeled isotope tags can be incorporated into the VICAT reagent (see Example I). The differential tags can be reacted with a test and control sample and run together or in parallel. The differentially labeled molecules can be analyzed using mass spectrometry (MS). Because the sample molecules are differentially labeled with light and heavy isotope tags, the peptide fragments can be distinguished by MS, allowing a side-by-side comparison of the relative amounts of each peptide fragment from a control sample and a test sample. If desired, MS can also be used to sequence the corresponding labeled peptides, allowing identification of molecules corresponding to the tagged peptide fragments.

Moreover, the use of an isotope tag in the VICAT reagent allows the incorporation of various heavy labels into the same molecule. A VICAT reagent having 0, +6 or +12 heavy isotopes is exemplified in FIGS. 1 and 2. By having chemically identical but differentially isotopically labeled VICAT reagents available, multiple tags can be used in the same experiment. For example, one VICAT reagent can be used to tag sample molecules, a second VICAT reagent can be used to tag a standard molecule for use as an internal standard, and a third VICAT reagent can be used as a marker for the sample molecule in a separation method. Thus, the ability to incorporate various amounts. of heavy isotope into an isotope tag provides versatility in the use of the VICAT reagent for labeling and isolating sample molecules, preparing standards, and visualizing sample molecules for isolation and analysis.

The use of multiple isotopic forms of the isotope tag of a VICAT reagent is advantageous for allowing tagging of a sample molecule, convenient localization of a sample molecule in a separation method, and quantification of the sample molecule by inclusion of an internal standard. As discussed above, a VICAT-labeled standard peptide can be added at relatively high quantities to facilitate localization in a separation method. The sample molecule can be labeled with the same VICAT reagent but with a differential tag, for example, a +6 tag. Furthermore, an internal standard labeled with still another differential tag, for example +12, can be included for quantification. In this case, one VICAT-labeled standard is added at a high concentration for visualization while a second VICAT-labeled standard is added in an amount suitable for quantifying the sample molecule. The internal standard added for quantifying the sample molecule is added in an amount suitable for quantification, that is, within the quantitative range of the detection method. One skilled in the art can readily determine an appropriate amount of internal standard to add to a sample for quantitative analysis and adjust the amount added depending on the type of quantitative analysis used. For example, the amount of internal standard can be adjusted so that the VICAT-labeled sample and standard molecules can be quantified by mass spectrometry. Similarly, one skilled in the art can readily determine a suitable amount of VICAT-labeled standard to use for visualization in a separation method depending on the nature of the detectable moiety on the VICAT reagent and the detection method used.

An advantage of the VICAT method is that a pair of peptides tagged with light and heavy VICAT reagents are chemically identical and therefore serve as mutual internal standards for accurate quantification (Gygi et al., supra, 1999). Using MS, the ratios between the intensities of the lower and upper mass components of pairs of heavy- and light-tagged fragments provides an accurate measure of the relative abundance of the peptide fragments. Furthermore, a short sequence of contiguous amino acids, for example, 5-25 residues, contains sufficient information to identify the unique polypeptide from which the peptide fragment was derived (Gygi et al., supra, 1999). Thus, the VICAT method can be conveniently used to identify differentially expressed molecules, if desired.

Furthermore, the methods of the invention are advantageous in that absolute quantification of a sample molecule can be determined if a known amount of VICAT-labeled standard molecule is included as a standard for quantitative analytical methods. The inclusion of a detectable tag in a VICAT reagent can be readily exploited to facilitate quantification and calibration of a VICAT-labeled standard. If a VICAT reagent contains a detectable moiety that absorbs light, the detectable moiety can be used to quantify a labeled molecule based on the absorption properties of the detectable moiety. Exemplary detectable moieties that absorb light include fluorophores such as coumarin. For example, if the detectable moiety absorbs in the ultraviolet (UV) range, UV absorbance can be used to determine the concentration of the labeled standard peptide. The concentration can be determined from Beer's law and the known extinction coefficient of the detectable moiety used in the VICAT reagent.

As discussed above, an isotope tag is included in a VICAT reagent, allowing differential labels to be incorporated into sample and standard molecules and facilitating quantification of sample molecules. Thus, a VICAT reagent can be used for two purposes, localization and quantification. The VICAT reagent is used to determine the location of a particular sample molecule based on visualization of the corresponding VICAT-labeled standard. The VICAT reagent also allows quantification by MS analysis based on the incorporation of isotopically distinct isotope tags, which can be used for quantitative comparison of the VICAT-labeled sample and standard molecules.

Although generally exemplified herein with the addition a standard peptide or peptides labeled with a corresponding isotopically labeled VICAT reagent for analysis of a particular sample polypeptide, it is understood that the methods of the invention are also applicable to the analysis of multiple sample polypeptides. For example, VICAT-labeled standard peptides can be added to identify and/or quantify two different polypeptides in a sample. In such a case, a particular VICAT reagent can be used to label sample polypeptides, and the corresponding standard peptides for the two polypeptides are labeled with an isotopically distinct version of the same VICAT reagent as used to label the sample polypeptides. The methods are advantageous in that multiple polypeptides in a sample can be analyzed.

Any number of different polypeptides in a sample can be analyzed so long as there is sufficient resolution of the standard VICAT-labeled peptides for further analysis. Thus, the methods of the invention can be used to identify and/or quantify three or more polypeptides in a sample, four or more polypeptides, five or more polypeptides, six or more polypeptides, seven or more polypeptides, eight or more polypeptides, nine or more polypeptides, ten or more polypeptides, twelve or more polypeptides, fifteen or more polypeptides, or even grater numbers so long as the VICAT-labeled peptides can be sufficiently resolved for further analysis. Corresponding VICAT-labeled standards for the multiple polypeptides to be analyzed can be synthesized and added to the sample.

When analyzing multiple polypeptides in a sample, a single VICAT reagent can be used to label sample polypeptides. In addition, more than one type of VICAT reagent can be used to label sample polypeptides. For example, one type of VICAT reagent can be used to label reactive sulfhydryl groups of sample polypeptides and a second type of VICAT reagent can be used to label reactive amine groups. The use of VICAT reagents having different reactive groups to label the same sample can be used to distinguish between two polypeptides. Furthermore, such VICAT reagents can also incorporate different detectable moieties, for example, two different fluorophores or chromophores. Thus, the use of different types of VICAT reagents containing different reactive groups and/or detectable moieties can be used to facilitate the identification and quantification of multiple polypeptides in a sample. One skilled in the art can readily determine suitable VICAT reagents for differential labeling of two or more polypeptides in a sample.

The methods of the invention can be used in a variety of applications. The methods of the invention are particularly useful for analysis of polypeptides for which antibodies are not available. For example, the methods can be used to analyze polypeptides for which antibodies have not been generated or which are poorly immunogenic. In the case where new gene sequences or splice variants are identified, there is no need to recombinantly express the encoded polypeptide for antibody production. Instead, only one or a few peptides that uniquely identify a polypeptide need to be synthesized, which can be readily predicted from the nucleic acid sequence.

The methods of the invention can also be applied to the quantification of specific isoforms of splice variants. The peptides selected as standards are chosen based on known or empirically determined splice variants. The peptide standards are selected such that, for each alternatively spliced protein, minimally one peptide is used that is common to all splice variants and minimally one peptide is used that is unique for each splice variant tested.

The methods can also be applied to the detection and quantification of proteins associated with genetic disease. As such, a genetic disease known to be associated with aberrant expression of a polypeptide can be analyzed using methods of the invention by including a VICAT-labeled peptide standard corresponding to the aberrantly expressed polypeptide.

An exemplary genetic disease for which methods of the invention can be applied is muscular dystrophy (see Example IV). Duchenne and Becker muscular dystrophies are allelic disorders caused by a deficiency of the dystrophin protein in muscle (Worton and Brooke, in *The Metabolic and Molecular Bases of Inherited Diseases*, 7th ed., Scriver, ed., ppl 4195-4112, McGraw-Hill, New York (1994)). The dystrophin gene, located on the X chromosome at Xp21, is one of the largest genes in the human genome (2,300 kb), contains 79 exons, and encodes a 427 kDa cytoskeletal protein. The dystrophin protein is missing in boys with Duchenne muscular dystrophy (DMD) and is significantly decreased in those with Becker muscular dystrophy (BMD).

From a diagnostic perspective, approximately ⅔ of affected males can be confirmed to have muscular dystrophy by molecular methods that can identify deletions or duplications within the dystrophin gene (Chamberlain et al., *Nucl. Acids Res.* 16:11141-11156 (1988)). Confirmatory diagnosis of DMD or BMD in the remaining ⅓ of patients who have small genetic alterations typically involves a surgical muscle biopsy with antibody staining or immunoblot analysis to show the absence of dystrophin. A truncated dystrophin revealed by immunoblot analysis, or an in-frame deletion in the central portion of the gene, would predict the Becker form of muscular dystrophy. The average cost associated with an open muscle biopsy and pathological evaluation exceeds $3000 and places children with muscular dystrophy at clinical risk from anesthesia, with the potential for rhabdomyolosis occurring from the anesthesia.

A VICAT reagent of the invention can be applied to quantitatively measure dystrophin from very small muscle samples that can be obtained by needle biopsy. Such methods are also applicable to other forms of muscular dystrophy. Thus, the VICAT reagents of the invention can be used in methods directed to microtechnology for the quantitative measurement of specific proteins in muscle tissue. In addition to diagnostic applications, the methods can also be applied to measuring the effectiveness of gene therapy or other therapies used to treat a disease.

The reagents and methods of the invention are also applicable to diagnosing and determining the prognosis for various cancers. For example, mRNA expression array experiments are performed on tumor samples of various tissues, for example, lung, colon, liver, ovary, breast, prostate, and the like. The mRNA expression experiments allow the determination of tumor-associated changes in gene expression, either up-regulation or down-regulation, compared to normal corresponding tissue. Furthermore, it is useful to determine whether any of the abberantly expressed proteins, particularly those having increased expression, are present in blood serum of the patients. If so, these up-regulated proteins can function as convenient markers for diagnosis of the corresponding cancer in serum samples from patients. Exemplary cancer diagnostic markers include prostate specific antigen (PSA) for prostate cancer and CA125 for ovarian cancer. The VICAT reagents and methods of the invention are particularly useful for rapidly screening "candidate" diagnostic markers by measuring the level of the corresponding protein in serum or other bodily fluids and determining whether the amount of candidate diagnostic markers correlate with the disease.

Thus, the invention provides a method of diagnosing a disease. The method can include the steps of contacting a sample from a patient with a VICAT reagent of the invention under conditions allowing the reactive group to bind to and react with one or more polypeptides in the sample, thereby labeling one or more polypeptides with the reagent; cleaving the polypeptides in the sample to generate peptide fragments; adding one or more peptide standards to the sample, wherein the peptide standards correspond to peptides generated from cleaving sample polypeptides, are labeled with an isotopically distinct version of the isotope tag, and are derived from a polypeptide exhibiting aberrant expression in the disease; resolving the labeled peptides in the sample; visualizing the labeled peptides; contacting the labeled peptides with a capture moiety for the affinity tag; isolating the labeled peptides; cleaving the linker of the reagent to release the isolated peptides; quantifying the released peptides; and comparing the amount of sample peptide to standard peptide in the released peptides, wherein the amount of sample peptide is correlated with the diagnosis of the disease. The methods can be used to diagnose a variety of diseases in which aberrant protein expression is associated with a disease, either increased or decreased expression.

The methods of the invention are particularly useful for diagnosis of genetic diseases, where one or a few aberrantly expressed proteins are diagnostic for a disease. For example, the methods can be used to diagnose a disease such as muscular dystrophy, including Duchenne muscular dystrophy or Becker muscular dystrophy by measuring decreased expression of dystrophin. Similarly, the methods of the invention can be used to quantify the expression of prostate specific antigen (PSA) for diagnosis of prostate cancer. One skilled in the art will readily recognize that the methods of the invention are applicable to these and other diseases associated with aberrant expression of one or more polypeptides. Furthermore, one skilled in the art can readily generate corresponding standard peptides for analysis of the aberrantly expressed polypeptides using methods of the invention.

Thus, one skilled in the art can readily apply the methods of the invention to the analysis of known markers associated with a disease. An increasing number of protein markers for a variety of diseases are becoming available through genomics and proteomics analysis. For example, mRNA expression arrays can be used to determine differential expression between a healthy individual and an individual having a disease. VICAT-labeled standards corresponding to the differentially expressed mRNAs can be synthesized and used for qualitative and/or quantitative diagnostic analysis of patient samples of the same tissue. Furthermore, if the differentially expressed mRNAs encode one or more secreted proteins or peptides, the methods of the invention can be applied to blood or serum samples to analyze differentially expressed secreted proteins correlated with a disease state.

The methods of the invention are also applicable to the detection and quantification of patterns of protein expression that are diagnostic or prognostic for a disease. The methods can be used in diagnostic applications in body fluids such as blood, serum or plasma, cerebrospinal fluid, urine, saliva, seminal plasma, pancreatic juice, breast milk, lung lavage, and the like. Because the methods can be used to analyze and quantify multiple peptides in the same analysis, the methods are particularly useful for diagnostic applications since the ability to analyze multiple polypeptides in the same analysis allows multiple peptides correlated with a diagnostic application to be used rather than the analysis of one diagnostic marker alone. Thus, the methods can be applied to the analysis of multiple diagnostic markers associated with a disease. Once a set of diagnostic markers has been identified, the methods of the invention can be applied to quantify the set of markers for an analysis that is expected to be more informative than the analysis of a single diagnostic marker alone.

Diagnostic patterns of protein expression can be determined by direct comparative, quantitative protein profiling of tissues or body fluids of persons afflicted with a particular disease and healthy control individuals (Gygi et al., *Nat. Biotechnol.* 17:994-999 (1999); WO 00/11208). Alternatively, diagnostic protein expression patterns can be determined from gene expression array measurements in afflicted tissue of an individual having a disease and healthy control tissue of the same type. In addition, specific marker proteins can be identified from known disease markers found in the scientific literature. One skilled in the art will recognize that these and other methods for determining or identifying differential protein expression correlated with a disease state can be used to identify protein disease markers suitable for diagnostic applications using VICAT reagents and methods of the invention.

The invention additionally provides a kit containing one or more VICAT reagents. For example, the kit can contain a single VICAT reagent useful for labeling and identifying a polypeptide. In addition, a kit can contain a set of two or more differentially isotopically labeled VICAT reagents, which is particularly useful for quantitative analysis using mass spectrometry. The contents of the kit of the invention, for example, one or more VICAT reagents, are contained in packaging material, and, if desired, a sterile, contaminant-free environment. In addition, the packaging material contains instructions indicating how the materials within the kit can be employed to label sample molecules. The instructions for use typically include a tangible expression describing the reagent concentration or at least one assay method parameter, such as the relative amounts of reagent and sample to be admixed, maintenance time periods for reagent/sample admixtures, temperature, buffer conditions, and the like.

It is understood that modifications which do not substantially affect the activity of the various embodiments of this invention are also provided within the definition of the invention provided herein. Accordingly, the following examples are intended to illustrate but not limit the present invention.

EXAMPLE I

Chemical Structure and Synthesis of VICAT Reagents

This example describes a synthetic scheme for VICAT reagents.

The structure of exemplary VICAT reagents and their corresponding synthetic schemes are-shown in FIGS. 1, 2 and 4. A representative reagent contains the biotin and iodoacetyl features that are present in the ICAT reagents (Gygi et al., Nature Biotechnol. 17:994-999 (1999) and also contains a tetramethylrhodamine to make the reagent highly colored and fluorescent. The iodoacetyl group is attached to an ethylenediamine unit, which is attached to the rest of the VICAT reagent via a photolabile 2-nitrobenzyloxycarbonyl group. Exposure of the VICAT-peptide conjugate to long wavelength UV light (using a handheld lamp) for several minutes leads to photocleavage of the bond between the benzyl carbon and the bridging ester oxygen, yielding Peptide-S—$CH_2CONHCH_2CH_2NH$—COOH. The latter undergoes spontaneous decarboxylation (Olejnik et al., *Proc. Natl. Acad. Sci. USA* 92:7590-7594 (1995) to yield Peptide-S—$CH_2CONHCH_2CH_2NH_2$. This peptide cysteine-bound N-aminoethylacetamido group is abbreviated NAMETAG.

Also shown in FIGS. 1 and 2 are the VICAT(+6) and VICAT(+12) reagents, which contain heavy isotopes in the NAMETAG portion, thus increasing their mass by +6 and +12, respectively. After photocleavage, the NAMETAG group, with or without isotopic substitution, is left on the peptide so that the peptides can be quantified by the ICAT-based method (Gygi et al., supra, 1999).

Three different peptides, 10-15 amino acids in length and containing a single NAMETAG-derivatized cysteine, were found to undergo normal peptide bond fragmentation during tandem ESI-MS. Thus, the presence of the NAMETAG does not interfere with obtaining peptide sequence information. Additionally, the amide in the NAMETAG moiety eliminates ethylenediamine upon collision-induced dissociation (CID)' which serves to fingerprint by MS/MS those peptides that contain the NAMETAG. The VICAT reagents also have the advantageous property of being water soluble at the concentrations needed for peptide mixture analysis. In particular, the presence of the tertiary amine in the linker will be protonated at pH near neutrality or lower and thus contribute to reagent solubility in water.

The NBD-VICAT reagent shown in FIG. 1A was synthesized as shown in FIG. 1B. Briefly, tetrahydrofuran (THF) was distilled from sodium metal/benzophenone ketyl. Methylene Chloride ($CH_2Cl_2$), and triethylamine (TEA) were distilled from $CaH_2$. Anhydrous dimethylformamide (DMF) and pyridine were purchased from Aldrich Chemical Co. (Milwaukee, Wis.). HPLC grade solvents were purchase from Fisher (Fair Lawn, N.J.). Water for HPLC was purified at point-of-use by a Milli-Q water system (Millipore, Bedford, Mass.). Trifluoroacetic acid (TFA) was purchased from Advanced ChemTech (Louisville, Ky.), (+)-Biotin, di-t-butyl dicarbonate, diethylenetriamine, ethylenediamine, and iodoacetic anhydride are from Aldrich Chemical Co. (Milwaukee, Wis.), and 4-Fluoro-7-nitrobenzofurazan (NBD-F) is from Dojindo Molecular Technologies, Inc. (Gaithersburg, Md.). All other reagents were used as received. Unless otherwise noted, all non-aqueous reactions were carried out under Argon atmosphere with oven-dried glassware.

For spectral analyses, NMR spectra were recorded on Bruker spectrometers: AC-200 (200 MHz), AC-300 (300 MHz) or AC-500 (500 MHz). In rare cases, NMR data had to be omitted for proteins that are likely to be buried under the NMR peak from the solvent. Mass spectral data was obtained using Bruker Daltonics (Bremen, Germany) Esquire electrospray-ion trap mass spectrometer.

For chromatography, silica gel flash chromatography was performed using 230-400 mesh silica gel 60 (Merck, Darmstadt, Germany). Thin-Layer chromatography was performed on silica 60 with F254, aluminum-backed plates (Merck). Reversed-phase HPLC separations were performed using a Vydac (Hisperia, Calif.) semi-preparative column (up to 5 mg total loading, 10 μm packing, 10 mm×250 mm, catalog no. 218TP1010) at 4 mL/min, or a preparative column (up to 300 mg total loading, 10 μm packing, 20 mm×250 mm, catalog no 218TP1022) at 6 mL/min.

Compound 1. (+)-Biotin (3 g, 12.3 mmol) was dissolved in warm anhydrous DMF (60 mL). After the reaction was cooled to room temperature, TEA (3.2 mL, 24.6 mmol) was added, followed by tetrafluorophenyl trifluoroacetate (4.85 g, 18.5 mmol, prepared according to the literature). After being stirred for 30 minutes at room temperature, the solvent was removed under reduced pressure. The residue was crystallized with diethyl ether, and the product filtered (compound 1). The solid was dried under vacuum to afford 3.9 g (81%) of a white solid. $^1$H-NMR (300 MHz, DMSO-$d^6$) δ 7.9 (m, 1H); 6.4 (2H, d); 4.2 (2H, dt); 3.2 (m, 1H); 2.75-2.9 (m, 3H), 2.6 (1H, d); 1.4-1.8 (m, 6H).

Compound 2. To a round bottom flask containing diethylenetriamine (5.5 g, 51 mmol) at 0° C. was transferred via cannula a solution of compound 1 (2 g, 5.10 mmol) in DMF (40 mL), also at 0° C. After being stirred for 30 min at 0° C., solvent was removed under reduced pressure. The resulting residue was crystallized with ethyl ether (100 mL), filtered, and washed with acetone (50 mL). The solid was left under vacuum overnight, and 1.2 g (71%) of the desired product was obtained (compound 2). $^1$H-NMR (300 MHz, DMSO-$d^6$) δ 6.4 (2H, d); 4.2 (2H, dt); 3.2 (m, 3H); 3.0-2.4 (m, 8H); 2.1 (t, 2H), 1.2-1.7 (m, 6H). ESI-MS $(M+H^+)^+$: 330.4, $(M+2H^+)^{2+}$: 659.4.

Compound 3. To a round bottom flask containing a solution of compound 2 (300 mg, 0.91 mmol) in DMF (30 mL) at 0° C. was slowly added a solution of di-t-butyl dicarbonate (200 mg, 0.91 mmol) in DMF (2 mL). After being stirred for an hour at 0° C., the ice bath was removed, and the reaction was left stirring overnight at room temperature. The solvents were concentrated under reduced pressure without heating. A mixture of ethyl ether and methylene chloride was added to the residue, and the resulting solution was stirred for 3-4 h. The final product was filtered, and dried under vacuum to afford a white solid (compound 3) (290 mg, 74.4%). $^1$H-NMR (300 MHz, DMSO-$d^6$) δ 6.4 (2H, d); 4.2 (2H, dt); 3.2 (3H, m); 3.0-2.4 (m, 8H); 2.1 (m, 2H), 1.2-1.7 (m, 15H). ESI-MS $(M+H^+)^+$: 430.5.

Compound 4. To a vial containing a solution of compound 3 (130 mg, 0.30 mmol) in DMF (3 mL) was added a solution of 5-bromomethyl-1-(1-hydroxyethyl)-2-nitrobenzene (prepared according to the literature method, the material used also contained 1 part in 4.6 of 5-methyl-1-(1-hydroxyethyl)-2-nitrobenzene)(160 mg) in DMF (1 mL), followed by TEA (86 μL, 0.62 mmol). The reaction mixture was stirred at room temperature for 7 days, and then placed in a shaker at 37° C. for 2 days. The solvents were removed in a speed-vacuum apparatus, and the reaction mixture was injected onto the HPLC column. Preparative $C_{18}$ column, detector λ=240 nm, A=$H_2O$ with 0.08% TFA, B=acetonitrile (MeCN) with 0.0806 TFA, gradient: 0'-20': 20% B; 20'-80': 100% B. Product (compound 4)(50 mg, 27%) came out at 44% B. $^1$H-NMR (300 MHz, MeOH-$d^4$) δ 8.05 (1H, s); 8.0 (1H, d); 7.7 (1H, d); 5.35 (1H, q); 4.5 (1H, dd); 4.25 (1H, dd); 3.6 (2H, bs); 3.45-3.25 (m, 8H); 3.2 (m, 1H); 2.95(1H, dd); 2.7(1H, d); 2.2 (2H, t); 1.8-1.25 (m, 6H); 1.5 (3H, d); 1.4 (9H, s). ESI-MS $(M+H^+)^+$: 609.5, $(M+Na^+)^+$: 631.5.

Compound 5. To a vial containing a solution of compound 4 (70 mg, 0.12 mmol) in a 1:1.75 mixture of DMF: $CH_2Cl_2$ (total volume of 550 μL) was added a solution of carbonyl diimidazole (28 mg, 0.17 mmol) in $CH_2Cl_2$ (850 μL). After being stirred at room temperature for 2 h in the presence of 4 angstrom molecular sieves, ethylenediamine (32 μL, 0.23 mmol) was added. After an additional 1.5 h, the solvent was removed in a speed-vacuum apparatus. The residue was injected onto the HPLC column. Preparative $C_{18}$ column, λ=240 nm, A=$H_2O$ with 0.08% TFA, B=MeCN with 0.08% TFA, gradient: 0'-20': 20% B; 20'-80': 100% B. Product (compound 5) as TFA salt (43.5 mg, 47%) came out at 40% B. First intermediate: ESI-MS (M+H$^+$)$^+$: 703.6, (M+Na$^+$)$^+$: 725.6; Final product 5: ESI-MS (M+H$^+$)$^+$: 695.7, (M+Na$^+$)$^+$: 717.7.

Compound 6. To a vial containing compound 5 (43.5 mg, 0.054 mmol) in THF (1 mL) in the presence of 4 angstrom molecular sieves, was added TEA (6 µL, 0.054 mmol), followed by a solution of iodoacetic anhydride (21 mg, 0.059 mmol) in THF (1 mL). After stirring for 1.5 h at room temperature, an excess of 1 equivalent of TEA and 0.5 equivalents of iodoacetic anhydride were added to the reaction mixture. After an additional 1.5 h at room temperature, the solvents were removed in a speed-vacuum apparatus. The residue was injected onto the HPLC column. Preparative $C_{18}$ column, λ=240 nm, A=H$_2$O with 0.08% TFA, B=MeCN with 0.08% TFA, gradient: 0'-20': 20% B; 20'-80': 100% B. Product (23.4 mg, 55%) came out at 49% B (compound 6). ESI-MS (M+H$^+$)$^+$: 863.7, (M+Na$^+$)$^+$: 885.6

Compound 7. To a vial containing a solution of compound 6 (23.4 mg, 0.027 mmol) in CHCl$_3$ (0.4 mL) was added TFA (80 µL). The reaction mixture was stirred for 1.5 h at room temperature. Solvent was removed using a speed-vacuum apparatus. Methanol (MeOH) was added, and the resulting solution was concentrated in the speed-vacuum apparatus. This procedure was repeated 3 more times to remove excess TFA. The TFA salt of the product (compound 7) was obtained in 98% yield (23.4 mg) as oil. ESI-MS (M+H$^+$)$^+$: 763.5.

Compound 8. To a vial containing compound 7 (10 mg, 0.011 mmol) was added a solution of NBD-F (7.2 mg, 0.027 mmol) in DMF (640 µL), followed by Hunnig's base (8 µL, 0.046 mmol). After being stirred at room temperature for 1 hr in the presence of 4 angstrom molecular sieves, the solvents were removed in a speed-vacuum apparatus. The residue was injected onto the HPLC column. Preparative $C^{18}$ column, λ=500 nm, A=H$_2$O, B=MeCN, gradient: 0'-20': 20% B; 20'-80': 100% B. An orange solid (compound 8)(4.6 mg, 43.8%) came out at 51% B. $^1$H-NMR (500 MHz, MeOH-d$^4$) δ 8.43 (1H, d); 7.6 (2H, bs); 7.45 (1H, d); 6.16 (1H, bs); 6.05 (1H, q); 36.8 (2H, bs); 3.65 (2H, m); 3.25-3.15 (m, 6H); 2.96-2.88 (6H, m); 2.8 (1H, t);. 2.71(1H, d); 2.22 (2H, t); 1.8-1.55 (4H, m); 1.5 (3H, d); 1.42 (12H, m). ESI-MS (M+H$^+$)$^+$: 926.6, (M+Na$^+$)$^+$: 948.7.

Other exemplary VICAT reagents can be readily synthesized by the route shown in FIG. 2. Briefly, biotin p-nitrophenyl ester is reacted with excess diethylenetriamine (both from Aldrich; Milwaukee Wis.) to give the mono-amide, which is purified by rapid silica gel chromatography using a simple 2-step solvent elution procedure. Reaction of an excess of this mono-amide with 5-carboxytetramethylrhodamine succinimidyl ester (Molecular Probes Inc.; Eugene Oreg.) gives the diamide, which is purified on a reverse-phase HPLC column. Both the triamine linker and the biotinylating reagent are inexpensive. Thus, the synthesis can be performed using the short synthetic route shown in FIG. 2, with the use of excess reagents (triamine in step 1 and mono-amide in step 2). Alternatively, a longer synthetic route involving linker protection and deprotection steps can be used.

The diamide is reacted with 1-(4-bromomethyl-2-nitrophenyl)-ethan-2-ol, which is prepared in 3 steps from commercially available 5-methyl-2-nitro-benzoic acid (Aldrich) (Senter et al, *Photochem. Photobiol.* 42:231-237 (1988)). This alkylation occurs preferentially on the secondary amine rather than on the carboxylate of the tetramethylrhodamine moiety. Based on analogous chemistry (Olejnik et al., supra, 1995), the benzyl alcohol moiety is reacted with N,N'-disuccinimidyl carbonate (Aldrich), and the active carbonate ester is reacted with ICH$_2$CONHCH$_2$CH$_2$NH$_2$ (prepared by reaction of BOC-ethylenediamine with iodoacetyl chloride followed by treatment with trifluoroacetic acid) to give the desired VICAT reagent.

Figure 4B:
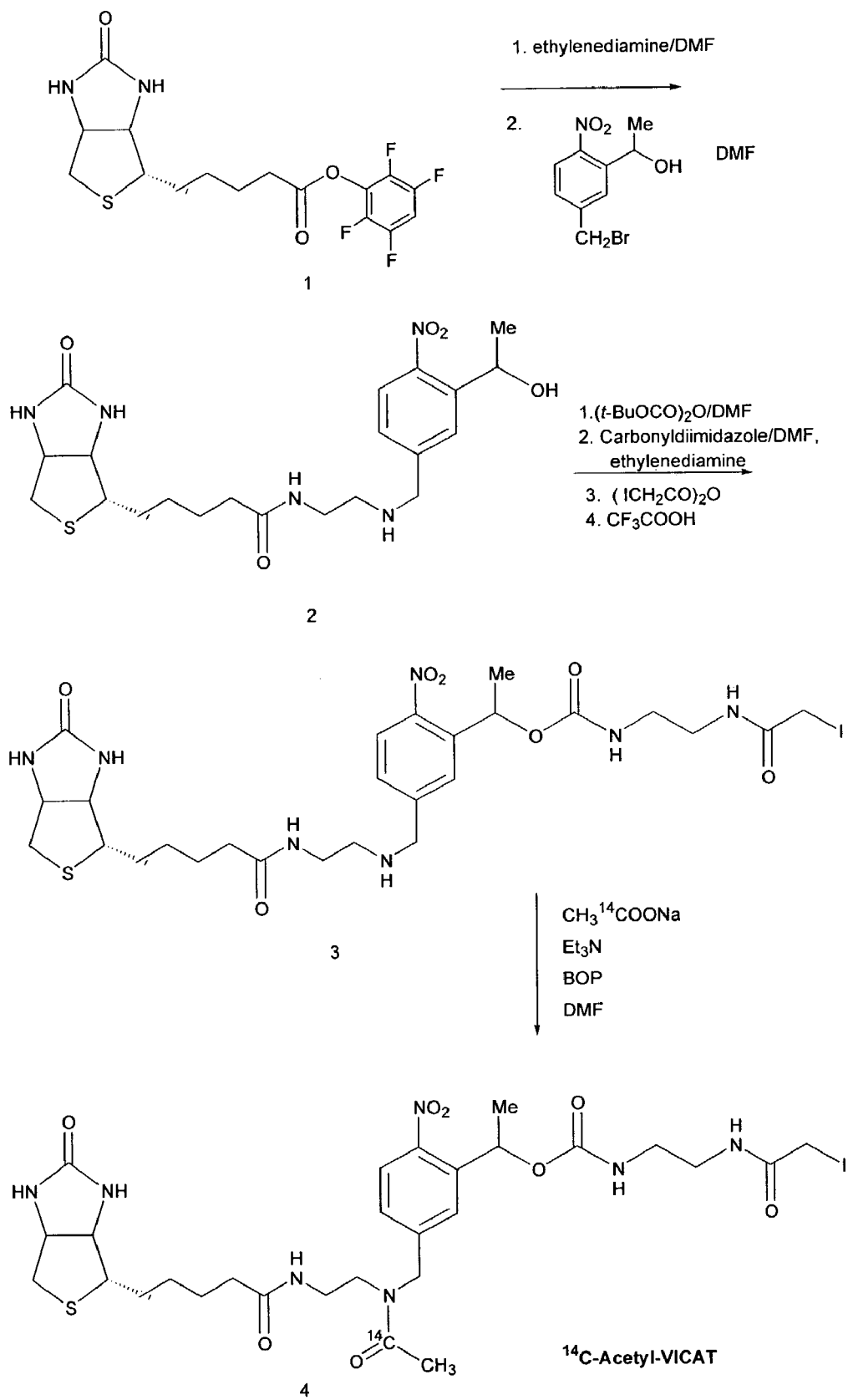
FIG. 4B shows a reaction scheme for the synthesis of $^{14}$C-Acetyl-VICAT.

Additional exemplary VICAT reagents can be readily synthesized by the route shown in FIG. 4B. The VICAT reagent shown in FIG. 4 is an exemplary VICAT reagent having a radioactive detectable moiety. The $^{14}$C-acetyl-VICAT reagent is synthesized (see FIG. 4B) in a manner substantially similar to that described above for other VICAT reagents. Briefly, compound 1 is reacted with ethylenediamine in DMF, followed by reaction with 5-bromomethyl-1-(1-hydroxyethyl)-2-nitrobenzene in DMF to generate compound 2. Compound 2 is reacted with di-t-butyl dicarbonate in DMF. To the product of this reaction is added carbonyldiimidazole in DMF, followed by ethylenediamine. To the product of this reaction is added iodoacetic anhydride, followed by TFA, to generate compound 3. Compound 3 is dissolved in DMF, and sodium 1-[$^{14}$C]acetate, TEA, and BOP (Benzotriazol-1-yloxytris(dimethylamino)phosphonium hexafluorophosphate) are added to generate compound 4 ($^{14}$C-acetyl-VICAT).

The isotopically labeled VICAT reagents are prepared as follows (FIGS. 1 and 2 insert). Di-$^{13}$C-labeled oxalic acid (Cambridge Isotopes; Andover Mass.) is distilled from ethanol/H$_2$SO$_4$ to give diethyl oxalate, which is treated with NH$_4$OH in ethanol to give di-$^{13}$C-labeled oxamate, ($^{13}$CONH$_2$)$_2$ (Wilmes and Winnewisser, *J. Labeled Compd. Radiopharm.* 31:1037-1040 (1992). The latter is reduced with LiAlD$_4$ (Aldrich) in tetrahydrofuran (THF) (Thomas, *Deuterium Labeling in Organic Chemistry*, Appleton-Century-Crofts, New York (1971)) to give H$_2$N$^{13}$CD$_2$$^{13}$CD$_2$NH$_2$. Repetition of this sequence of chemical reactions using $^{15}$NH$_4$OH (Cambridge Isotopes)(excess $^{15}$NH$_3$ can be fully recovered by bulb-to-bulb distillation) gives H$_2$$^{15}$N$^{13}$CD$_2$$^{13}$CD$_2$$^{15}$NH$_2$.

The labeled ethylenediamines is reacted with di-t-butyldicarbonate to give the mono-BOC derivatives (Lochner et al., *Helv. Chim. Acta* 81:2270-2281 (1998)). Di-$^{13}$C-labeled acetic acid (Cambridge Isotopes) is heated in D$_2$O/K$_2$CO$_3$ for 3-5 h at 120° C. (Atkinson et al., *J. Am. Chem. Soc.* 90: 498-499 (1968)) to give $^{13}$CD$_3$$^{13}$COOD, which is reacted with phosphorus and Br$_2$ to give Br$^{13}$CD$_2$$^{13}$COBr (Ward, *J. Chem. Soc.* 1160-1165 (1922)). The labeled bromoacetyl bromide is reacted with the BOC-protected ethylenediamine, followed by BOC removal with trifluoroacetic acid, to give Br$^{13}$CD$_2$$^{13}$CO$^{15}$NH$^{13}$CD$_2$$^{13}$CD$_2$$^{15}$NH$_2$, which is treated with KI in acetone to give the desired I$^{13}$CD$_2$$^{13}$CO$^{15}$NH$^{13}$CD$_2$$^{13}$CD$_2$$^{15}$NH$_2$ (12 atomic mass units (amu) higher than the non-isotopically substituted compound). Likewise, the +6 amu shifted compound ICH$_2$CONH$^{13}$CD$_2$$^{13}$CD$_2$NH$_2$ is prepared in the same way. All of these reactions proceed in near quantitative yield and make use of relatively inexpensive heavy isotopelabeled materials. The conversion of H$_2$NCH$_2$CH$_2$NH$_2$ to ICH$_2$CONHCH$_2$CH$_2$NH$_2$ is obtained in 80% overall yield with non-labeled materials.

This example describes a synthetic method for generating VICAT reagents.

EXAMPLE II

Labeling, Detection and Cleavage of a Peptide Sample

This example describes a procedure for labeling protein samples with VICAT reagents.

Cell or tissue protein are reduced, and cysteine-containing proteins are tagged with a VICAT reagent. The sample is submitted to proteolysis, for example, with trypsin, to generate the peptide mixture. The proteolytic digestion can be carried out, for example, overnight at a suitable temperature for the protease used, such as 22-37° C. for trypsin. A defined amount of one or more internal standards, peptides tagged with isotopically substituted VICAT reagent, are added to the proteolytic digest. These internal standards are readily prepared by solid-phase synthesis of the peptides of interest (matching in sequence to the peptides generated by proteolysis of the proteins of interest) and reacting the cysteine of these synthetic peptides with the isotopically heavy VICAT reagent.

The peptide mixture derived from the biological sample is subjected to isoelectric focusing (TEF) in a polyacrylamide gel strip. An adjacent IEF strip is loaded with the same internal standard that was added to the complex protein mixture. Both IEF strips are developed side-by-side, and visual inspection of the strip containing internal standard alone reveals the precise locations of the chemically identical VICAT-tagged peptide in the adjacent IEF strip containing the complex peptide mixture. The appropriate region of this latter strip is sliced from the strip, and peptides in these slices are eluted with suitable solvents, for example, 10 mM ammonia, 30% $CH_3CN$. Other elution solvents can be used, as desired, for example, aqueous buffer with detergent, chaotropic agents, and the like, or organic solvents, which can be used to elute peptides having low solubility in aqueous solution. Elution yields can be monitored by the fluorescence of VICAT-peptide conjugates. The eluted sample mixture is neutralized, if desired, and bound to streptavidin agarose. The VICAT-labeled and bound peptide is released by photocleavage from the solid phase matrix, resulting in free labeled peptide, also called NAMETAG-peptide.

Alternatively, a relatively large amount of one or more internal standards can be chromatographed in a single IEF strip with the sample of interest. Large amounts of these internal standards are provided so that they can be visualized above a background of VICAT-tagged, sample-derived peptides. These visualized markers are tagged with, for example, the +12 VICAT reagent so they can be distinguished from the internal standard bearing, for example, a +6 VICAT tag and the peptide coming from the example bearing, for example, the +0 VICAT tag.

The eluted tagged-peptides are subjected to photocleavage to cleave the VICAT reagent from the peptide, generally so that most of the VICAT reagent is cleaved. Photocleavage results in only a small fragment, which bears the isotopic substitution, being retained on the cysteine SH of the peptide. The resulting peptides are analyzed, for example, using tandem ESI-MS. Because the complex protein mixture also contains a known amount of peptide standard tagged with isotopically substituted VICAT reagent, integration of the ion signals from the heavy and light peptide conjugates allows accurate quantification of the peptide of interest (see Gygi et al., supra, 1999). In addition, peptide identification can be obtained by mass spectrometric sequencing of the ESI-produced ions by collision-induced dissociation (CID). Other mass spectrometric methods can also be used for the detection, quantification and identification of the tagged peptides, based on the fact that the precise mass and sequence of the tagged peptide are known.

Using the above described method with VICAT reagents that contain a fluorescent or chromophoric detectable group, all cysteine-containing peptides in the complex cell-derived mixture are made visible by tagging with the VICAT reagent. However, visual localization is generally carried out only for the IEF strip that bears the standard alone. Using chemically identical, fluorophore-containing tags for chromatographic marker, internal standard, and sample-derived peptides ensures identical chromatographic behavior. In addition to using adjacent IEF strips run side-by-side, a single strip containing two sample lanes can also be used. Furthermore, the VICAT-labeled standard can be added directly into the sample as an internal standard, particularly when differential isotope VICAT reagents are available, such as the +0, +6, and +12 reagents, as described above. The differentially labeled peptides are expected to co-migrate since it has previously been shown that ICAT-labeled proteins precisely co-migrate in two-dimensional gels (IEF/SDS-PAGE (sodium dodecyl sulfate polyacrylamide gel electrophoresis))(Smolka et al., *Mol. Cell. Proteomics* 1:19-29 (2002)).

Using the above described method with VICAT reagents that contain a radioactive detectable group, all cysteine-containing peptides in the complex cell-derived mixture are made visible by tagging with the VICAT reagent in a substantially similar manner to that described above for fluorescent or chromophoric detectable groups. For example, standard and sample can be run in parallel gels or parallel lanes on the same gel. The use of a radioactive detectable group allows the convenient addition of the standard to the same gel strip or even directly into the sample being analyzed, with localization of a particular sample molecule determined by detection of the radiolabel of the corresponding standard.

The above-described method using an internal standard can be used to determine the absolute amount of sample peptide in the biological sample. To calculate the amount of sample protein from the amount of peptide, the efficiency of proteolytic generation of the peptide is determined. Alternatively, the amount of sample-derived peptide can be compared to that of a control sample, if desired.

This example describes a general protocol for the use of a VICAT reagent to label proteins in a sample.

EXAMPLE III

Isoelectric Focusing and ESI-MS Analysis of Peptides

This example describes the analysis of peptides labeled with a VICAT reagent using isolectric focusing and ESI-MS.

The peptide mixture consisting of the tagged peptides from the protein sample mixture and the differentially isotopically tagged internal standard are often very complex and need to be separated prior to ESI-MS analysis. Any of a number of peptide separation methods can be applied to the sample, for example, chromatography, electrophoresis, and the like. Among the multitude of mature peptide separation methods available, isoelectric focusing (IEF) in polyacrylamide gels with immobilized pH gradients is particularly useful for the following reasons: i) The method is robust, relatively inexpensive, highly reproducible and easily multiplexed (Righetti et al., *Methods. Enzymol.* 270:235-55 (1996)). IEF strips covering different pH ranges are commercially available (for example, Pharmacia-Amersham Biotech; Piscataway N.J.); ii) The method has immense separation power (Righetti et al., supra, 1996), and the pH gradient, and therefore the range of maximal separation, can be tuned, as desired for particular experimental applications; iii) The pI of peptides can be reasonably well calculated from their amino acid sequences (Bjellqvist et al., *Electrophoresis* 14:1023-1031 (1993)); thus, the migration position of a specific target peptide-VICAT conjugate in the gel can be predicted, allowing rational choice of the pH range of the IEF used values. The tetramethylrhodamine group of the VICAT. reagent will be zwitterionic when the pH equals the pI for most peptides, and thus the peptide and VICAT-peptide conjugate will have similar pI values. Furthermore, the pI value of the VICAT-peptide conjugate can be calculated using the pKa value of the COOH group of the tetramethylrhodamine; and vi) Peptide recovery is achieved in high yield simply by soaking the gel segment in an appropriate solvent such as an aqueous buffer.

For analysis of peptide samples by IEF, a peptide sample generated by tryptic digestion, or other suitable protease digestion, of the VICAT-labeled protein sample essentially as described in Example II (see also Gygi et al., supra, 1999). Internal standard peptide(s) are added to the VICAT-labeled digest with soluble carrier ampholytes to a final concentration of 0.5% and applied to a rehydration cassette (Pharmacia-Amersham Biotech). The gel is allowed to swell for 4 h. The gel strips are transferred to the electrophoresis chamber and focused at a final voltage of 8000V for a total of 115,000 volt-hours. The voltage is slowly ramped up to avoid peptide precipitation and local overheating of the gel. A second identical gel strip is loaded with the external tagged peptide standard(s) alone for the localization of the target peptide(s) in the gel. The gel strips are subjected either to visual inspection or to fluorescence imaging, if needed for increased sensitivity. The gel segments containing the target peptide(s) are extracted and the isolated peptides are bound to the affinity matrix. The affinity isolated peptides are subjected to photocleavage to remove the fluorescent tag and release the NAMETAG-peptides having the isotopic label. The peptide-NAMETAG conjugates are analyzed by combined microbore-HPLC/ESI-MS using the standard protocols and software tools developed for quantitative protein profiling by the ICAT method (Han et al., *Nat. Biotechnol.* 19:946-951 (2001); Gygi et al., supra, 1999).

If the affinity reagent is avidin, the extracted peptides are bound to streptavidin modified agarose. beads or streptavidin modified magnetic beads using standard protocols and washed. NAMETAG peptides are recovered from the solid support by photo cleavage of the linker. The beads re resuspended in of 0.2 M Tris, pH 8.0, 10 mM EDTA with 2% β-mercaptoethanol to prevent methionine oxidation during photo-cleavage. Light from a Blak-Ray longwave UV lamp (VWR) is filtered by 10% of copper (II) sulfate solution (1 cm path length) and used to illuminate the beads for 2 hours. Beads are occasionally agitated to ensure uniform light illumination. The recovered peptides are analyzed by LC-MS/MS using the standard protocols and software tools developed for quantitative protein profiling (Gygi et al., supra, 1999; Han et al., *Nat. Biotechnol.* 19:946-951 (2001)).

This example describes protocols for IEF and ESI-MS analysis of VICAT-labeled peptides.

EXAMPLE IV

Dystrophin Analysis Using VICAT Reagents

This example describes the use of the VICAT technology for the quantification of dystrophin and its structural variants, which is clinically relevant for the diagnoses of Duchenne's and Becker's muscular dystrophy.

The distribution of pI values for the full set of cysteine-containing, tryptic peptides derived from the human proteome is calculated. With current genome annotation, ~33,000 proteins are predicted, giving ~230,000 cysteine-containing, tryptic peptides. It is expected that far fewer proteins will be expressed in any given cell type. The distribution of pI values is not uniform; clusters of up to a few thousand peptides exist. Thus, it is useful to search for those dystrophin-derived peptides that will migrate in the IEF strip in a noncrowded region. There are 8 dystrophin-derived, cysteine-containing, tryptic peptides that will migrate in relatively non-crowded regions containing <50 peptides. Also, the pH gradient in the crowded regions can be flattened, providing better separation.

The VICAT method allows selective detection of segments of dystrophin, which is useful for the diagnosis of variants of muscular dystrophy caused by dystrophin deletions. The amount of dystrophin present in total skeletal muscle protein can also be determined. Initial studies are carried out with the crude surface membrane fraction prepared from skeletal muscle using a simple 3-step differential centrifugation procedure (Ohlendieck et al., *J. Cell Biol.* 112:135-148 (1991)). Approximately 1% of the total protein in this fraction is dystrophin, whereas this protein constitutes 0.002% of total skeletal muscle protein (Ohlendieck and Campbell, *FEBS Lett.* 283:230-234 (1991)). A 100 mg sample of skeletal muscle obtained by needle biopsy contains ~0.5 μg of dystrophin (~1 pmol), which is more than sufficient for analysis. For example, 10-50 fmol of peptide can be routinely detected when this amount is applied to microbore-HPLC/ESI-MS system.

For analysis of dystrophin in muscle sample, proteins in the membrane fraction are solubilized by boiling in 50 mM Tris-HCl, pH 8.3, 5 mM EDTA, and either 0.5% SDS or 0.05% SDS/6 M urea. These buffers have been shown to work well for ICAT analysis of microsomal proteins (Han et al., *Nat. Biotechnol.* 19:946-951 (2001); Smolka et al., *Anal. Biochem.* 297:25-31 (2001)). Protein disulfides are reduced by treatment with 5 mM tributyl phosphine for 30 min at 37° C. (Smolka et al., supra, 2001), and cysteines are tagged with 200 nM to 1 mM VICAT reagent, depending on the amount of peptides in the sample to be analyzed, for 90 min at room temperature. The sample is diluted 10-fold to reduce the concentration of denaturants, a known amount of internal standard (for example, synthetic dystrophin peptide tagged with VICAT(+6)) is added, and the sample is treated with trypsin overnight at 37° C. VICAT-peptide conjugates can be isolated using solid-phase, monomeric avidin as described previously for ICAT reagents (Gygi et al., supra, 1999). IEF and microbore-HPLC/ESI-MS are carried out as described above. If peptide sample and IEF marker are run in separate lanes of the same IEF strip, the VICAT(+12) reagent can optionally be used to prepare the IEF marker in case some of it diffuses into the adjacent IEF lane containing the peptide mixture. Alternatively, the VICAT-labeled peptide standards are added to the sample molecules for resolution in a single IEF lane.

Alternatively, following reaction of sample peptides with a VICAT reagent, salt and detergent are removed by ion exchange chromatography, such as cation exchange chromatography, and step elution. This step can also serve to exchange the buffer composition for further manipulations. VICAT-labeled peptides in the sample mixture are resolved by IEF. The location of VICAT-labeled sample peptides are visualized using VICAT labeled standard peptides resolved in parallel or as an internal standard added to the sample mixture. Resolved VICAT-labeled peptides of interest are absorbed onto streptavidin beads. Photocleavage is carried out on the affinity isolated peptides, resulting in release of NAMETAG-peptide conjugate(s), which contain the isotope tag. The released NAMETAG-peptide conjugate(s) are analyzed by LC-MS/MS. Digestion with a protease such as trypsin can optionally be included at various steps, such as before or after reacting with the VICAT reagent, before or after resolving sample molecules, or before or after binding to the affinity resin.

The quantification of dystrophin using VICAT reagents can be carried out using mouse skeletal muscle. Frozen tissue is commercially available (Pel-Freeze Inc.; Rogers Ariz.). Of the 20 cysteine-containing, tryptic peptides of >5 amino acidsderived from dystrophin, 16 have identical sequences for mouse and human proteins, and 4 have nearly identical sequences. Skeletal muscle from the mdx mouse, which lacks dystrophin, can also be used (Sicinski et al., *Science* 244: 1578-1580 (1989)). After validation of the VICAT assay using mouse tissue, human muscle samples are obtained using Institutional Review Board approved protocols and analyzed as described above.

This example describes the analysis of dystrophin using a VICAT-reagent.

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A reagent comprising an affinity tag (A), a detectable moiety (D), a linker (L), an isotope tag (T), and a reactive group (R) having the general formula:

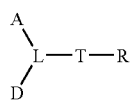

wherein said reactive group is attached to said isotope tag by a covalent bond, wherein said isotope tag is attached to said linker by a covalent bond, wherein said affinity tag is attached to said linker by a covalent bond, and wherein said detectable moiety is attached to said linker by a covalent bond, wherein said linker links said affinity tag and said detectable moiety to said isotope tag in the configuration shown in said formula, wherein the detectable moiety is radioactive and comprises a radioactive atom selected from the group consisting of $^3$H, $^{14}$C, $^{32}$P, $^{35}$S and $^{125}$I.

2. The reagent of claim 1, wherein said linker is cleavable.

3. The reagent of claim 1, wherein said affinity tag is selected from the group consisting of biotin, d-iminobiotin, N-biotinyl-sarcosine, glutathione, maltose, poly(His), and an epitope tag.

4. The reagent of claim 1, wherein said reactive group is selected from the group consisting of a sulfhydryl reactive group, an amine reactive group, and a carboxyl reactive group.

5. The reagent of claim 1, wherein said reagent has the structure

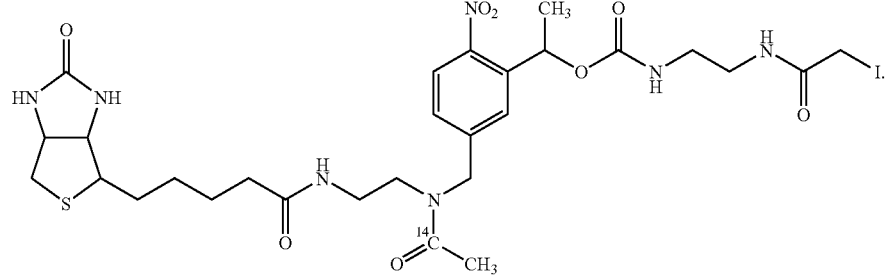

6. The reagent of claim 1, wherein the radioactive atom is $^3$H.

7. The reagent of claim 1, wherein the radioactive atom is $^{14}$C.

8. The reagent of claim 1, wherein the radioactive atom is $^{32}$P.

9. The reagent of claim 1, wherein the radioactive atom is $^{35}$S.

10. The reagent of claim 1, wherein the radioactive atom is $^{125}$I.

11. A reagent comprising an affinity tag, a detectable moiety, a cleavable linker, an isotope tag, and a reactive group, wherein said reactive group is attached to said isotope tag by a covalent bond, wherein said isotope tag is attached to said cleavable linker by a covalent bond, wherein said affinity tag is attached to said cleavable linker by a covalent bond, and wherein said detectable moiety is attached to said cleavable linker by a covalent bond, wherein said cleavable linker links said affinity tag and said detectable moiety to said isotope tag in a configuration whereby cleavage of said cleavable linker separates said affinity tag and said detectable moiety from said isotope tag and wherein said isotope tag remains covalently bonded to said reactive group, wherein said reagent has the structure

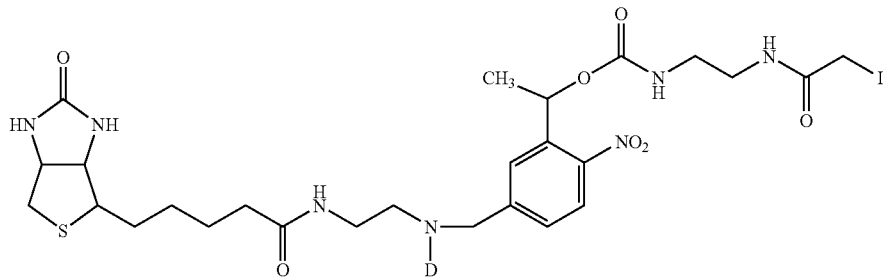

wherein D is a detectable moiety.

12. The reagent of claim 2, wherein said linker comprises a photocleavable moiety, a chemically cleavable moiety, or an enzymatically cleavable moiety.

13. The reagent of claim 3, wherein said affinity tag is biotin.

14. The reagent of claim 3, wherein said affinity tag is d-iminobiotin.

15. The reagent of claim 3, wherein said affinity tag is N-biotinyl-sarcosine.

16. The reagent of claim 3, wherein said affinity tag is glutathione.

17. The reagent of claim 3, wherein said affinity tag is maltose.

18. The reagent of claim 3, wherein said affinity tag is poly(His).

19. The reagent of claim 3, wherein said affinity tag is an epitope tag.

20. The reagent of claim 4, wherein said reactive group is a sulfhydryl reactive group.

21. The reagent of claim 4, wherein said reactive group is an amine reactive group.

22. The reagent of claim 4, wherein said reactive group is a carboxyl reactive group.

23. The reagent of claim 12, wherein said linker comprises a photocleavable moiety.

24. The reagent of claim 12, wherein said linker comprises a chemically cleavable moiety.

25. The reagent of claim 12, wherein said linker comprises an enzymatically cleavable moiety.

26. The reagent of claim 11, wherein the detectable moiety is a fluorophore or chromophore.

27. The reagent of claim 11, wherein said reagent has the structure

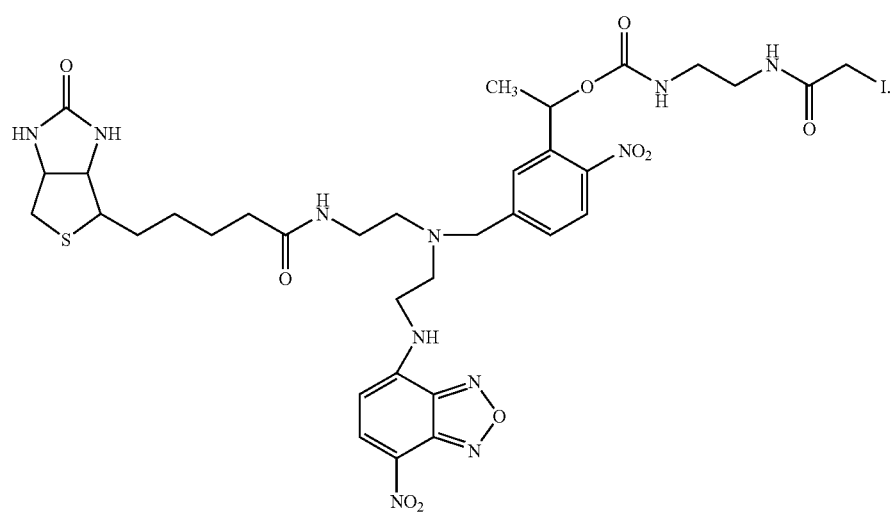

28. The reagent of claim 11, wherein said reagent has the structure

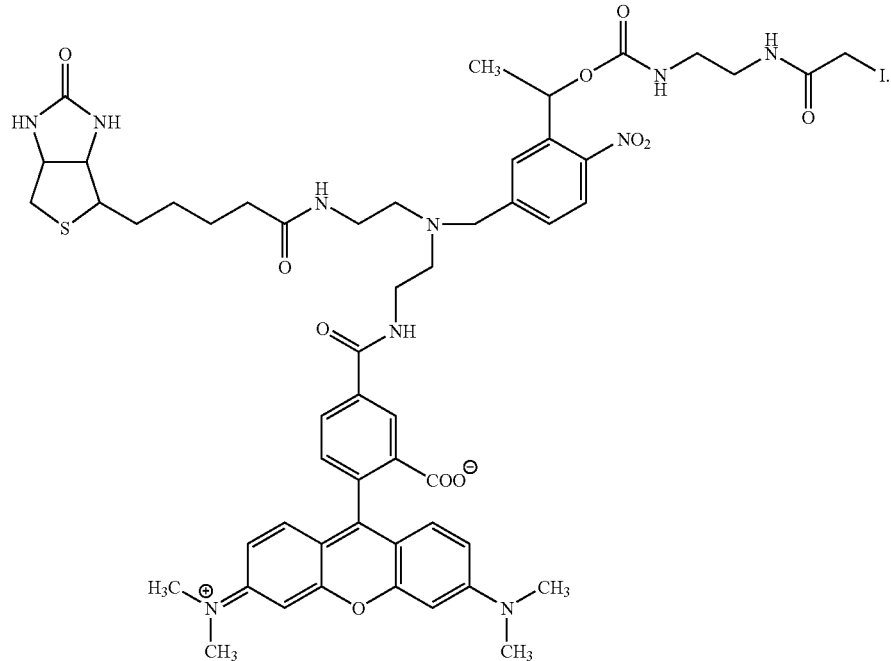

29. The reagent of claim 26, wherein said detectable moiety is a fluorophore.

30. The reagent of claim 26, wherein said detectable moiety is a chromophore.

31. The reagent of claim 29, wherein said fluorophore is selected from a rhodamine, a fluorescein, a napthalene, a coumarin, a pyrene, a pyridyloxazole and a dapoxyl.

32. The reagent of claim 31, wherein said fluorophore is a rhodamine.

33. The reagent of claim 31, wherein said fluorophore is a fluorescein.

34. The reagent of claim 31, wherein said fluorophore is a napthalene.

35. The reagent of claim 31, wherein said fluorophore is a coumarin.

36. The reagent of claim 31, wherein said fluorophore is a pyrene.

37. The reagent of claim 31, wherein said fluorophore is a pyridyloxazole.

38. The reagent of claim 31, wherein said fluorophore is a dapoxyl.

* * * * *